US010617167B2

(12) United States Patent
Baldi

(10) Patent No.: US 10,617,167 B2
(45) Date of Patent: Apr. 14, 2020

(54) VENTILATED MODULAR DUAL SHELLED HELMET SYSTEM

(71) Applicant: Apalone, Inc., Peoria, IL (US)

(72) Inventor: Steven T. Baldi, Peoria, IL (US)

(73) Assignee: Apalone, Inc., Peoria, IL (US)

( * ) Notice: Subject to any disclaimer, the term of this patent is extended or adjusted under 35 U.S.C. 154(b) by 228 days.

(21) Appl. No.: 15/820,256

(22) Filed: Nov. 21, 2017

(65) Prior Publication Data

US 2018/0153246 A1 Jun. 7, 2018

Related U.S. Application Data

(60) Provisional application No. 62/425,397, filed on Nov. 22, 2016.

(51) Int. Cl.
*A42B 3/12* (2006.01)
*A42B 3/28* (2006.01)
*A42B 3/10* (2006.01)
*A63B 71/10* (2006.01)
*A61F 7/10* (2006.01)
*A42B 3/04* (2006.01)
*A61F 7/02* (2006.01)
*A61F 7/00* (2006.01)

(52) U.S. Cl.
CPC ............... *A42B 3/285* (2013.01); *A42B 3/04* (2013.01); *A42B 3/10* (2013.01); *A61F 7/10* (2013.01); *A63B 71/10* (2013.01); *A61F 2007/0002* (2013.01); *A61F 2007/0008* (2013.01); *A61F 2007/0233* (2013.01); *A61F 2007/0238* (2013.01)

(58) Field of Classification Search
CPC ................................. A42B 3/121; A42B 3/285
See application file for complete search history.

(56) References Cited

U.S. PATENT DOCUMENTS

| | | | | |
|---|---|---|---|---|
| 2,625,683 A * | 1/1953 | Roth Herman P | ...... | A42B 3/12 2/6.1 |
| 4,133,055 A * | 1/1979 | Zebuhr | ................... | A42B 3/121 2/411 |
| 4,354,284 A * | 10/1982 | Gooding | ................... | A42B 3/00 2/413 |
| 6,397,399 B1 * | 6/2002 | Lampe | ................... | A42B 1/008 2/171.2 |
| 8,117,677 B2 * | 2/2012 | Toth | ....................... | A42B 3/285 2/413 |
| 8,938,817 B1 | 1/2015 | Baldi | | |
| 8,943,617 B2 * | 2/2015 | Harty | ..................... | A42B 3/285 2/468 |
| 9,220,311 B1 | 12/2015 | Baldi | | |
| D758,669 S | 6/2016 | Collette et al. | | |
| D764,116 S | 8/2016 | Collette et al. | | |

(Continued)

*Primary Examiner* — Tajash D Patel
(74) *Attorney, Agent, or Firm* — Howard & Howard Attorneys PLLC

(57) ABSTRACT

A modular helmet is described herein. The module helmet includes an inner shell adapted to be positioned onto a user's head and an outer shell coupled to the inner shell. The outer shell is spaced a distance radially outward from the inner shell to define a climatic zone between the inner shell and the outer shell. A cooling assembly is positioned within the climatic zone between the inner shell and the outer shell. The cooling assembly includes a plurality of cooling packets that are coupled to the outer shell.

18 Claims, 26 Drawing Sheets

(56) References Cited

U.S. PATENT DOCUMENTS

2012/0233774 A1\* 9/2012 Zerhusen ............ A61G 7/0507
　　　　　　　　　　　　　　　　　　5/425
2015/0223549 A1\* 8/2015 Osterhout ............ A42B 3/285
　　　　　　　　　　　　　　　　　　62/3.1

\* cited by examiner

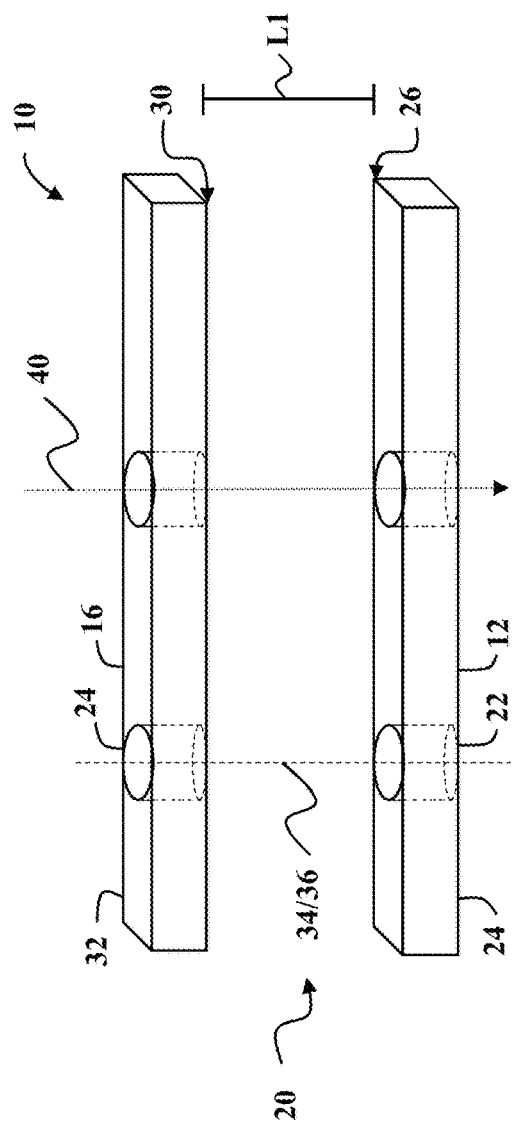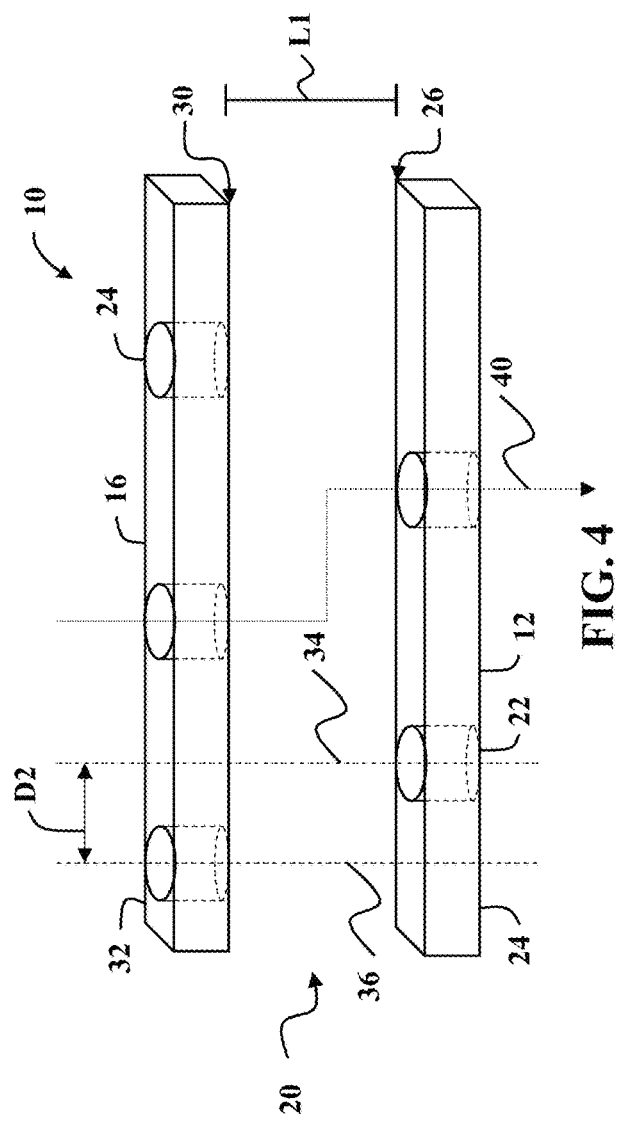

VENTILATED MODULAR DUAL SHELLED HELMET SYSTEM

CROSS-REFERENCE TO RELATED APPLICATION

This application claims priority to U.S. Provisional Patent Application Ser. No. 62/425,397, filed Nov. 22, 2016 which is hereby incorporated by reference in its entirety.

BACKGROUND OF THE INVENTION

1. Field of the Invention

This present invention relates to helmet assemblies, and more specifically, to helmet assemblies that include a ventilated modular shell system (VMS) that may be used in sports and activities, including military activities, that require the protection of a helmet and are conducted in high temperature environments.

2. Description of the Related Art

A continuous effort should be made to eliminate heat stroke deaths associated with activities requiring the use of a helmet, in particular American football. The Annual Survey of Football Injury Research published by National Center for Catastrophic Sport Injury states 24 football related heat stroke fatalities were documented during the 15-year period from 1986 to 2000. During the subsequent 15-year period from 2001 to 2015, 42 football related heat stroke fatalities were documented, a 175% increase. It has been noted helmets do not affect physiological parameters other than the local skin temperature and sweat rate. Heat loss from the head is one quarter to one third of total metabolic body heat. This is substantially higher than the head's proportion of the total body surface area. Thus the head has considerable heat loss capacity. Related to this is the National Athletic Trainers Association position the participants who wear equipment that does not allow for heat dissipation are at an increased risk for heat illness. Wearing a helmet is also a potential risk factor because a significant amount of heat is dissipated through the head. Another issue with current helmets is that the helmets are not resistant law impact. For example, a football player that repeatedly received minor hits to the head. Coaches desire the players to wear the actual gear they will play in to train as realistically as possible. As such, there is a need for a helmet that allows athletes to become acclimated to wearing the appropriate gear while not exposing themselves to exertional heatstroke.

The present invention is aimed at one or more of the problems identified above.

SUMMARY OF THE INVENTION

In one embodiment, a modular helmet is provided. The module helmet includes an inner shell adapted to be positioned onto a user's head and an outer shell coupled to the inner shell. The outer shell is spaced a distance radially outward from the inner shell to define a climatic zone between the inner shell and the outer shell. A cooling assembly is positioned within the climatic zone between the inner shell and the outer shell. The cooling assembly includes a plurality of cooling packets that are coupled to the outer shell.

In another embodiment, a modular helmet is provided. The modular helmet includes an inner shell adapted to be positioned onto a user's head, an outer shell, and a cushion assembly. The inner shell includes a plurality of inner vents. The outer shell is coupled to the inner shell and spaced a distance radially from the inner shell to define a climatic zone between the inner shell and the outer shell. The outer shell includes a plurality of outer vents configured to couple the climatic zone in flow communication with ambient air. The cushion assembly is positioned within the climatic zone between the inner shell and the outer shell. The cushion assembly includes a plurality of cushions that are coupled to the outer shell.

In a further embodiment, a fastening assembly for use with a helmet assembly including an outer shell is provided. The fastening assembly includes an outer support member adapted to be positioned within a support opening extending through the outer shell. The outer support member includes a base portion defining a pivot axis and a support arm extending outwardly from the base portion. The support arm is configured to contact an inner surface of the support opening to facilitate resisting a rotation of the helmet outer shell about the pivot axis.

BRIEF DESCRIPTION OF THE FIGURES

Non-limiting and non-exhaustive embodiments of the present invention are described with reference to the following figures. Other advantages of the present disclosure will be readily appreciated, as the same becomes better understood by reference to the following detailed description when considered in connection with the accompanying drawings wherein:

FIG. 3 illustrates a sectional view of a portion of the ventilated modular helmet system including coaxially oriented vents;

FIG. 4 illustrates a sectional view of a portion of the ventilated modular helmet system including off-set vents;

Corresponding reference characters indicate corresponding components throughout the several views of the drawings.

DETAILED DESCRIPTION OF THE INVENTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

The following detailed description of the present invention references the accompanying drawing figures that illustrate specific embodiments in which the invention can be practiced. The embodiments are intended to describe aspects of the present invention in sufficient detail to enable those skilled in the art to practice the invention. Other embodiments can be utilized and changes can be made without departing from the spirit and scope of the present invention the present invention is defined by the appended claims and, therefore, the description is not to be taken in a limiting sense and shall not limit the scope of equivalents to which such claims are entitled.

An aspect of the invention generally pertains to a ventilated modular helmet system that can decrease the effects of atmospheric heat related to sports activities and decrease the incidence of exertional heatstroke.

Another aspect of the invention generally pertains to a ventilated modular helmet system that creates a microclimate that is conducive to heat dissipation and accelerated sweat evaporation.

Yet another aspect of the invention generally pertains to ventilated modular helmet system that when worn with the optional padding can decrease the effects of regular impacts inherent to sports and decrease the incidence of concussions experienced by active participants.

The present invention provides a ventilated modular system (VMS) 10 that uses the external cushioning system, currently known as the modular dual shell helmet system (MDS) as its platform. The VMS includes a highly ventilated modular dual shelled helmet system that can be used in sports and activities, including military activities that require the protection of a helmet and are conducted in high temperature environments. In light of the prior art is significant that the VMS helmet has significantly more ventilation to allow for convection and evaporation. The VMS helmet also allows for the interchange of a highly ventilated outer practice shell for a full contact game shell without incurring the cost of purchasing an entirely new helmet. The VMS system allows a safer, cooler helmet that can be precisely modeled to match the game helmet in both size and weight.

Figure 1:
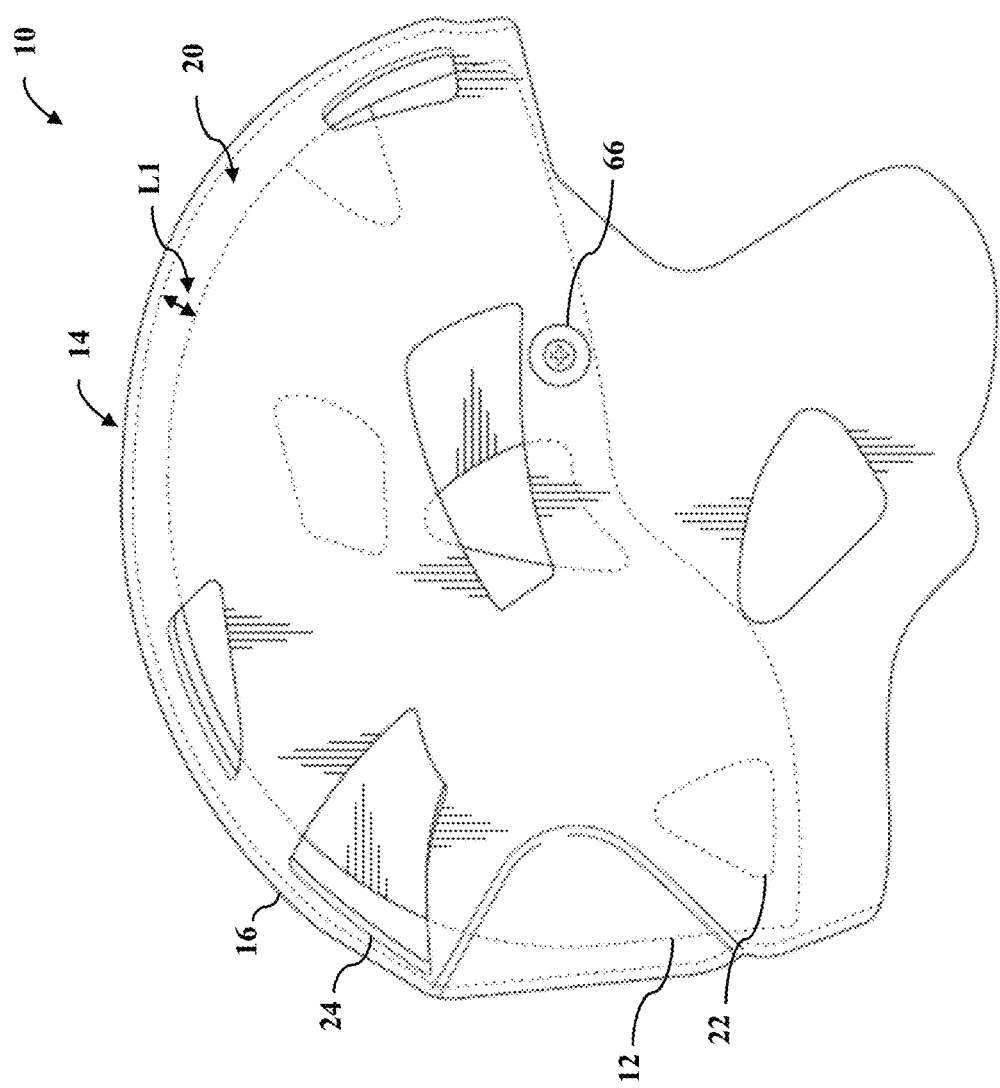
FIG. 1 is a side view of one embodiment of the ventilated modular helmet system in accordance with the teachings of the present disclosure.
Figure 2:
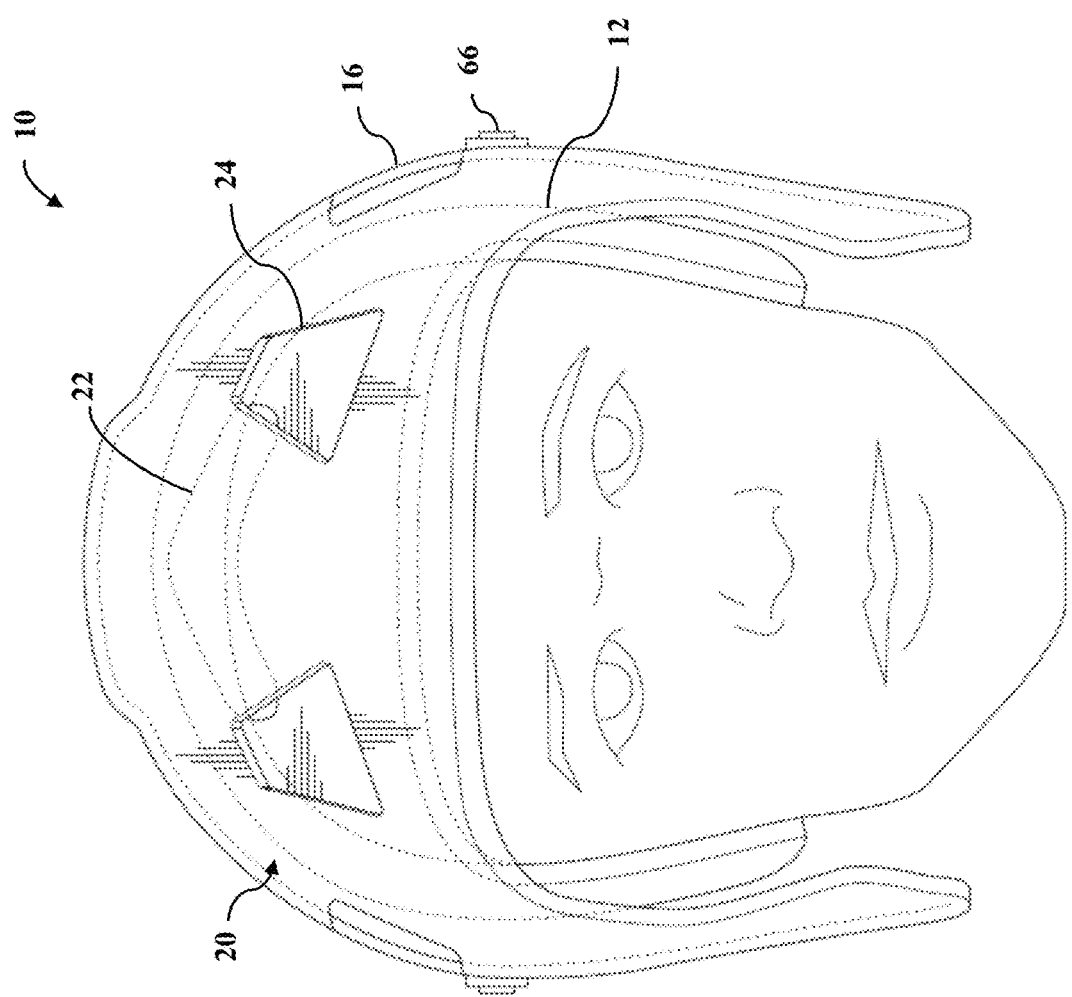
FIG. 2 is a front view of another embodiment of the modular ventilated helmet system in accordance with the teachings of the present disclosure.

In various embodiments, as illustrated in FIGS. 1 and 2, the ventilated modular helmet system (VMS) 10 for cooling includes an inner shell 12 and a cooling apparatus 14 coupled to the inner shell 12. The cooling apparatus 14 includes an outer shell 16 coupled to the inner shell 12 and a cooling assembly 18 (not shown). In one embodiment, the cooling apparatus 14 is configured to be coupled to an outer surface of a user's helmet. In the illustrated embodiment, the outer shell 16 is coupled to the inner shell 12 and spaced a distance radially outward from the inner shell 12 to define a climatic zone 20 between the inner shell 12 and the outer shell 16. The cooling assembly 18 is positioned within the climatic zone 20 between the inner shell 12 and the outer shell 16. In one embodiment, the inner shell 12 includes a plurality of inner vents 22 that extend through the inner shell body 12, an inner surface 24, and an outer surface 26. The inner vents 22 are configured to couple the climatic zone 20 in flow communication with an area adjacent to the user's head. In addition, the outer shell 16 may include a plurality of outer vents 28 that extend through the outer shell 16 an inner surface 30, and an outer surface 32. The outer vents 28 are configured to couple the climatic zone 20 in flow communication with ambient air. In one embodiment, at least one inner vent 22 may be aligned coaxially with a corresponding outer vent 28. In addition, one or more inner vents 22 may be aligned offset a distance from a corresponding outer vent 28.

The inner shell 12 is made out of a flexible material, a semi rigid material, or a rigid material. The flexible material may be easily displaced and act more as a membrane to distribute the applied forces if the system 10 is used with the plurality of cushions. The flexible material may have sufficient elasticity such that it returns to its original shape when deformed upon impact. The material used for the inner shell 12 may include but is not limited to any material having the desired physical properties. For example, the desired physical properties for the inner shell 12 may be made from polymers, plastics, thermoplastics, PVC, vinyl, nylon, or other similar materials. The materials used for the inner shell 12 may include materials that have a smooth outer surface and a high level of mar-resistance. These desired physical properties may reduce the drag coefficient that occurs between two helmets when they collide helping to reduce rotational forces generated through friction that may cause trauma and influence the probability of neck injury. A low drag coefficient also maximizes air flow through the plurality of inner vents 22, increasing the air movement and the evaporation within the climatic zone 20.

The outer shell 16 may be made out of a flexible material, a semi rigid material, or a rigid material. The flexible material may be easily displaced and act more as a membrane to distribute the applied forces if the system 10 is used with the plurality of cushions. The flexible material may have sufficient elasticity such that it returns to its original shape when deformed upon impact. The material used for the outer shell 16 may include but is not limited to any material having the desired physical properties. For example, the desired physical properties of the outer shell 16 may include polymers, plastics, thermoplastics, PVC, vinyl, nylon, or other similar materials. The materials used for the outer shell 16 may include materials that have a smooth outer surface and a high level of mar-resistance. These desired physical properties may reduce the drag coefficient that occurs between two helmets when they collide, or between the outer shell 16 and the surrounding air. This helps reduce rotational forces generated through friction that may cause trauma and influence the probability of neck injury. A low drag coefficient also maximizes air flow through the plurality of vents (described herein), increasing the air movement and the evaporation within the climatic zone 20. Unlike traditional helmets, the outer shell 16 of the VMS 10 provides shade to the inner shell 12 allowing a natural lowering of the temperature of the inner shell 12. Further mitigating the inherent heat absorption associated with single shell helmets, which place the exposed outer shell in direct proximity to the head. In addition, the outer shell 16 may be coated with a reflective material. The reflective material may prevent the absorption of solar energy by the outer shell 16 from light that may enter through the pores or the vents.

Figure 6:
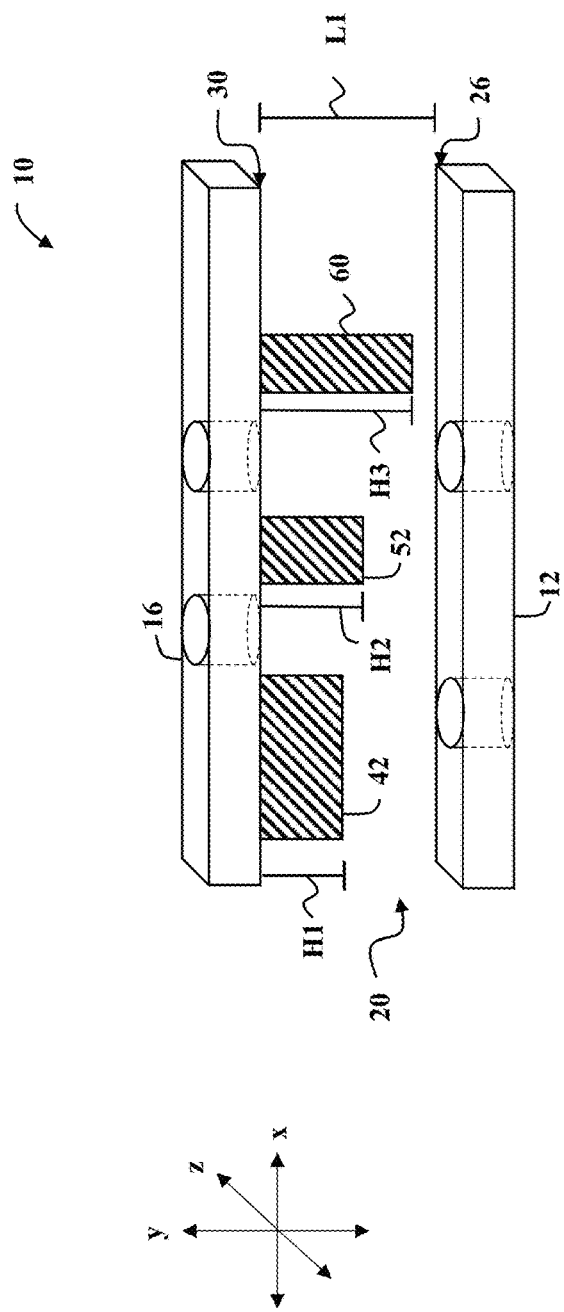
FIG. 6 illustrates another sectional view of a portion of the ventilated modular helmet system showing a cushion assembly and a cooling assembly.

With reference to FIGS. 3 and 4, on one embodiment, one or more inner vents 22 may be aligned coaxially with a corresponding outer vent 28. The inner vents 22 each have a center axis 34 and the outer vents 28 each have a center axis 36. In addition, one or more inner vents 22 may be aligned off-set a predetermined distance D2 from a center-line of a corresponding outer vent 24. The inner and outer vents are spaced along an x-axis within the inner shell 12 and the outer shell 16, respectively. As shown in FIG. 3, the inner and outer vents are aligned along the same center axis 34/36 along the y-axis allowing the air to travel from outside of the outer shell 16 through the outer vents 28 into the climatic zone 20. From the climatic zone 20, the air may then exit the climatic zone 20 through the inner vents 22 into the area adjacent to the user's head. In one embodiment, as shown in FIG. 4, the inner vents 22 may be aligned offset from the outer vents 28 along the x-axis. For example, each inner vent 22 and outer vent 28 may have a centerline axis 34/36. The centerline axis 34 of each inner vent 22 may be offset the predetermined distance D2 along the x-axis from the centerline axis 36 of a corresponding outer vent 28. The predetermined distance D2 is the distance between the center axis 36 of the outer vent 28 and the center axis 34 of the next preceding inner vent 22 on the inner shell 12. As shown in FIG. 6, the off-set vents allow the air that enters from the outside of the outer shell 16 to flow over the cooling assembly 20, cooling the air before reaching the user's head from the inner vents 22. This allows the air inside of the VMS 10 to be cooled, therefore cooling the head of the person using the helmet. The air is also able to move from inside of the VMS 10 through the inner shell 12 and the outer shell 16 to the outside of the VMS 10, allowing warmer air to leave the VMS 10.

In one embodiment, the plurality of inner vents 22 includes a first amount of inner vents and the plurality of outer vents 28 includes a second amount of outer vents that is a different amount than the first amount of inner vents. For example, the inner shell 12 may include 5 inner vents 22 and the outer shell 16 may include 6 outer vents 28.

Figure 5:
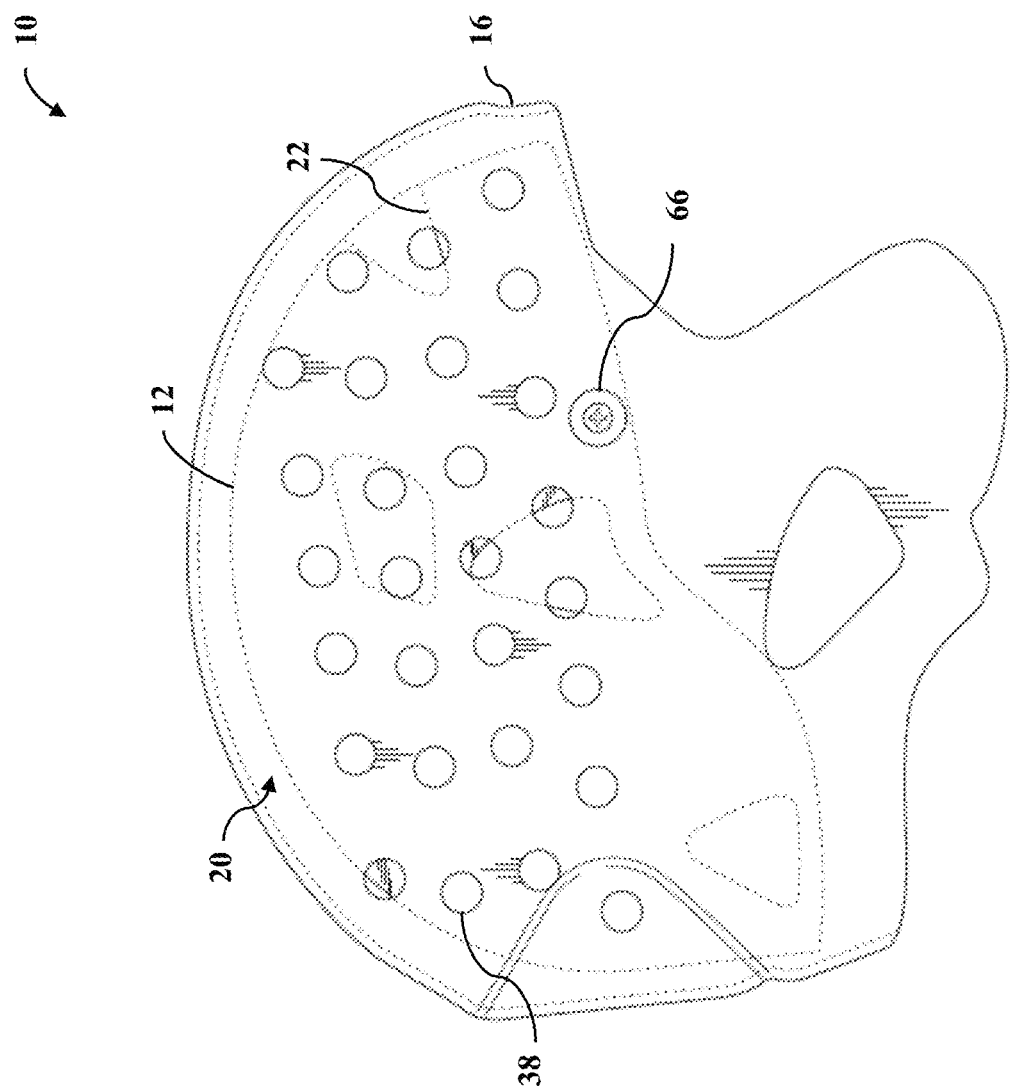
FIG. 5 is a side view of the ventilated modular helmet system of FIG. 1 including various embodiments of the present disclosure.

In one embodiment, as shown in FIG. 5 the outer shell 16 may include a plurality of pores 38. The replacement of the vents with pores is to prevent injuries. For example, each pre 38 may be sized and shaped to prevent a user's finger to enter into the pore opening thereby preventing the user's fingers from being caught in the pore opening. The pore 38 includes a minute opening on the surface of the outer shell 16 that allows gases, liquids, or microscopic particles to pass through the pore 38. Similar to the outer vents 28, the pores 38 may be oriented coaxially with a corresponding inner vent 22. In addition, the pores 38 of the outer shell 16 may be oriented off-set a predetermined distance along the x-axis from the inner vents 22. In one embodiment, the inner shell 12 may include a plurality of pores 38 (not shown).

In the illustrated embodiment, the climatic zone 20 is defined between the inner shell and the outer shell. As shown in FIG. 6, the distance of the climatic zone 20 is the length L1 along the y-axis between the inner surface 30 of the outer shell 16 and the outer surface 26 of the inner shell 12. The length of the climatic zone L1 may vary depending on the goals of the user. For example, FIGS. 1 and 2 show the VMS 10 without any additional components positioned within climatic zone 20. The length L1 is variable to maximize air movement within the climatic zone 20 that may enhance evaporation. When the climatic zone 20 does not include the cooling assembly 18, the climatic zone 20 passively allows an arid layer of air to form between the inner shell 12 and the outer shell 16. As shown by the arrows with broken lines in FIGS. 3 and 4, a flow 40 of air may move freely through the VMS 10. The ambient air may move straight from the outer vents 28 to the oriented corresponding inner vent 22, or the ambient air may move from at least one outer vent 28 to an off-set inner vent 22. The dryer atmosphere created by the empty climatic zone 20 with the arid layer of air provides a driving force to allow for the evaporation of perspiration from the athletes head. This allows for the natural cooling of the user's head.

Figure 7:
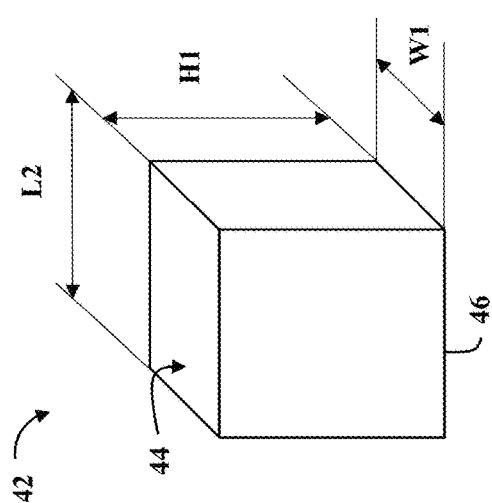
FIG. 7 illustrates a perspective view of a cooling packet that may be used with the cooling assembly.

As shown in FIG. 6, the climatic zone 20 may include the cooling assembly 18 that includes a plurality of cooling packets 42. The cooling assembly 18 includes the plurality of cooling packets 42 that are coupled to the inner surface 30 of the outer shell 16. The cooling assembly 18 may also be coupled to the inner shell 12 (not shown). Illustrated in FIG. 7, each cooling packet includes height H1 measured along a y-axis perpendicular to the inner surface 30 of the outer shell 16, a length L2 measured along an x-axis, and a width W1 measured along a z-axis. The height H1 is measured along the y-axis and is defined by the distance between the end 44 of the cooling packet 42 that is coupled to the inner surface 30 of the outer shell 16 and the end opposite 46 the side coupled to the outer shell 16. In one embodiment, each cooling packet 42 may include the same height. In another embodiment, one or more cooling packets may have different heights. In addition, the height H1 may vary depending on the goals of the VMS system 10. The length L2 is the distance of the cooling packet that runs parallel to the outer shell 16 along the x-axis. The width W1 is the thickness of the cooling packet 42 that extends along the z-axis. In one embodiment, each cooling packet may include similar lengths and widths. In another embodiment, one or more cooling packets 42 may include a different length and/or a different width. In addition, each cooling packet 42 may include a substantially similar shape. In another embodiment, one or more cooling packets 42 may include a different shape. The cooling packets 42 may include, but are not limited to, rechargeable cooling packs or desiccant packs. The positioning of the cooling packets 42 on the outer shell 16 may vary. The cooling packets 42 may be oriented coaxially with the inner vents 22 or one or more cooling packets 42 may be off-set from the inner vents 22 along the x-axis. The cooling packets 42 may also contain a solid, a gas, a liquid, or any substance that serves to lower the temperature of the surrounding environment of the cooling assembly. In addition, the cooling packets 42 may be positioned by removing an attachment mechanism (described herein), separating the inner shell 12 and the outer shell 16, and directly placing the pad in the desired location via adhesion, Velcro™, and/or the existence of a predetermined slot (not shown) that may facilitate securing the cooling packet 42 to the outer shell 16.

Figure 8:
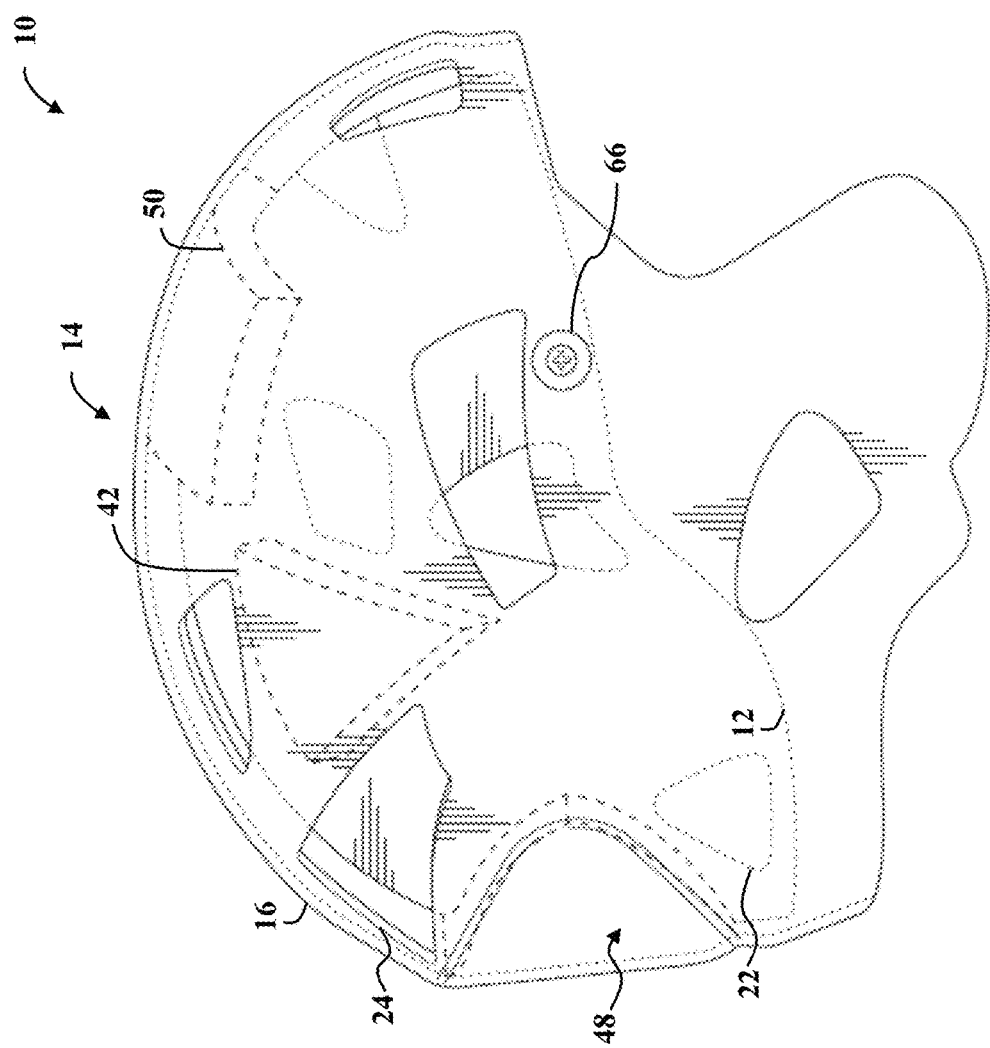
FIG. 8 is a side view of the ventilated modular helmet system of FIG. 1 including various embodiments of the disclosure.
Figure 9:
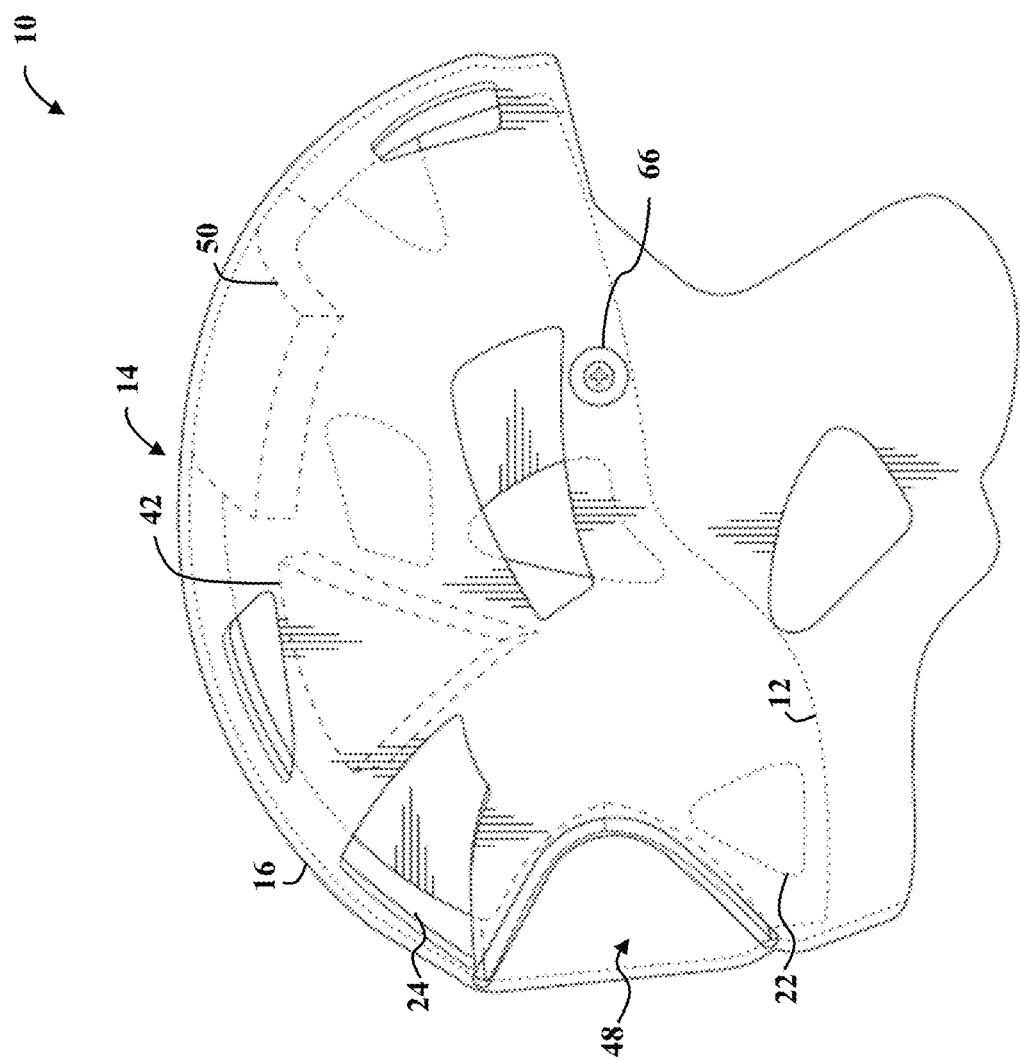
FIG. 9 is the side view of the ventilated modular helmet system of FIG. 1 indicating the cooling packet insertion slot.

In one embodiment, shown in FIGS. 8 and 9, the outer shell 16 includes at least one opening 48 that allow the placement and retention of the cooling packet 42 without the separation of the inner shell 12 and the outer shell 16. The cooling packets may be placed in the predetermined slots through the opening 48. The opening 48 is protected by a removable cover (not shown). The cooling packet 42 is rechargeable by nature, allowing it to be regenerated between practices or activities. After use, the cooling packets 42 may be removed and re-frozen. Once the player is ready to play and use the helmet (VMS 10), the cooling packets 42 may then be placed inside the opening 48 in the predetermined slots. The weight of a football uniform increases metabolic rate, which increases heat production, and its inherent insulation reduces heat dissipation to the surrounding air, which decreases heat loss. These dual properties lead to greater thermal and cardiovascular strain in hot environments. When environmental conditions warrant, a cold water or ice tub and ice towels should be available to immerse or soak a patient that is suspected to have the heat illness. These two points demonstrate the risk football players are at when training in the heat and the benefits of cooling their enclosed environment, for instance the environment inside of the player's helmets. The cooling packet 42 may lower the impact heat retention caused by the uniform by lowering the temperature within the helmet while simultaneously improving the conduction. Conduction is the transfer of heat from warmer to cooler objects through direct physical contact. Heat loss from the head is one-quarter to one-third of the total metabolic body heat. This is substantially higher than the heads proportion total body surface area. The cooling packet 42 being placed inside the VMS 10 may diminish the overall probability of exertional heat illnesses.

In another embodiment, the cooling packet 42 may include a solid, a liquid, a gas, or any substance that may act as a desiccant. The desiccant may be a hygroscopic substance that induces or sustains a state of dryness (desiccation) in its vicinity. The placement of a rechargeable desiccant packet 50 in the cooling assembly 18 produces an ideal environment for evaporation. Evaporation is the most efficient means of heat transfer. The heat is transferred via the vaporization of sweat. The evaporation of sweat from the skin depends on the water saturation of the air and the velocity of wind speed. For example, the ventilated modular system 10 allows air movement in the football helmet to further cool the athlete. The VMS 10 establishes a microclimate that induces air movement away from the high humidity of the scalp and pulls the moisture to the surface. This allows the increase of the evaporation of sweat and resulting in an increase in heat transfer away from the athlete's head. The increase in heat transfer decreases the core body temperature resulting in a decreased probability of exertional heat injury.

Figure 10:
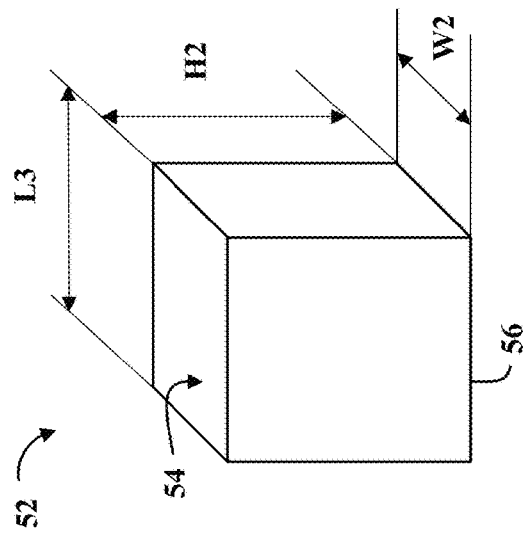
FIGS. 10 and 11 are perspective views of a cushion that may be used with the cushion assembly.
Figure 11:
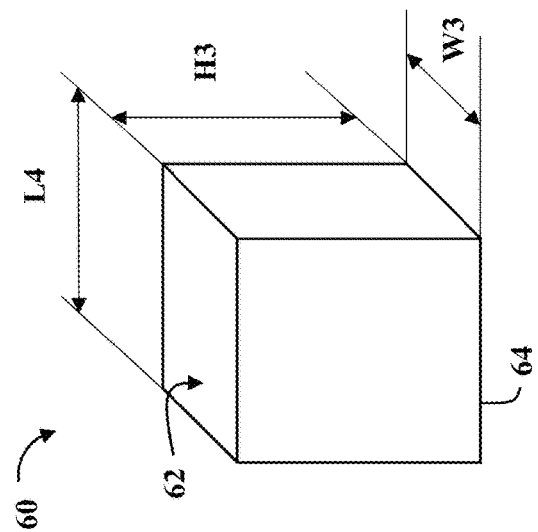
Figure 12:
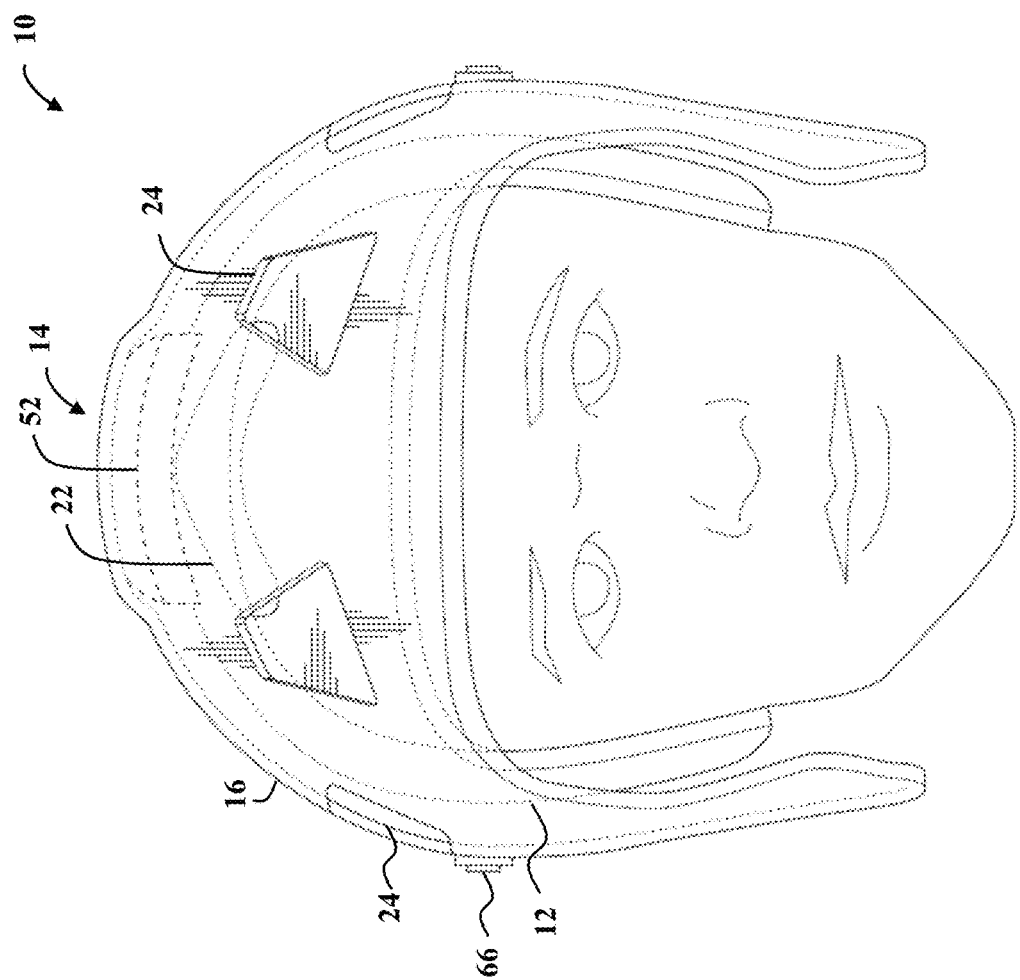
FIG. 12 is a front view of the ventilated modular helmet system of FIGS. 8 and 9 with the various components in place.
Figure 13:
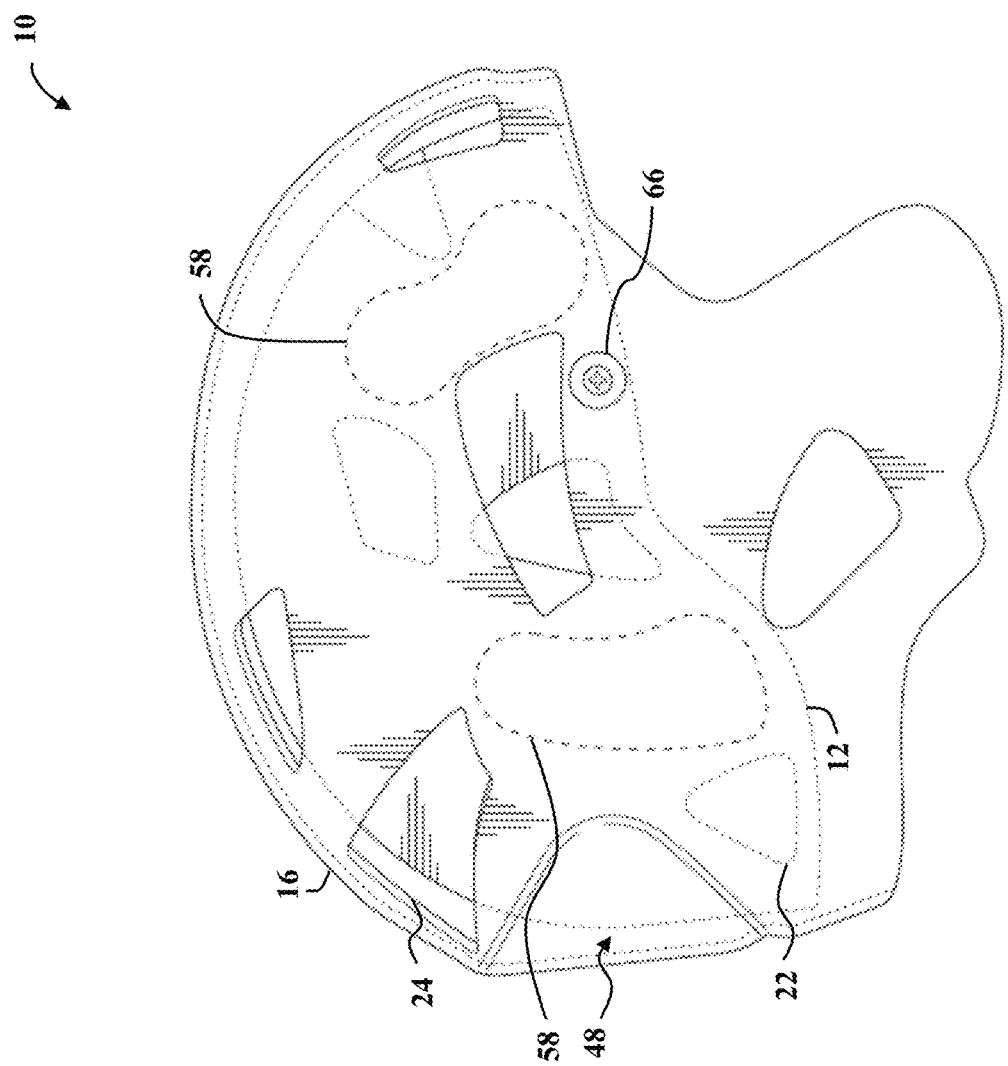
FIG. 13 is another side view of the ventilated modular helmet system of FIG. 1 with only the optional cushions in place.
Figure 14:
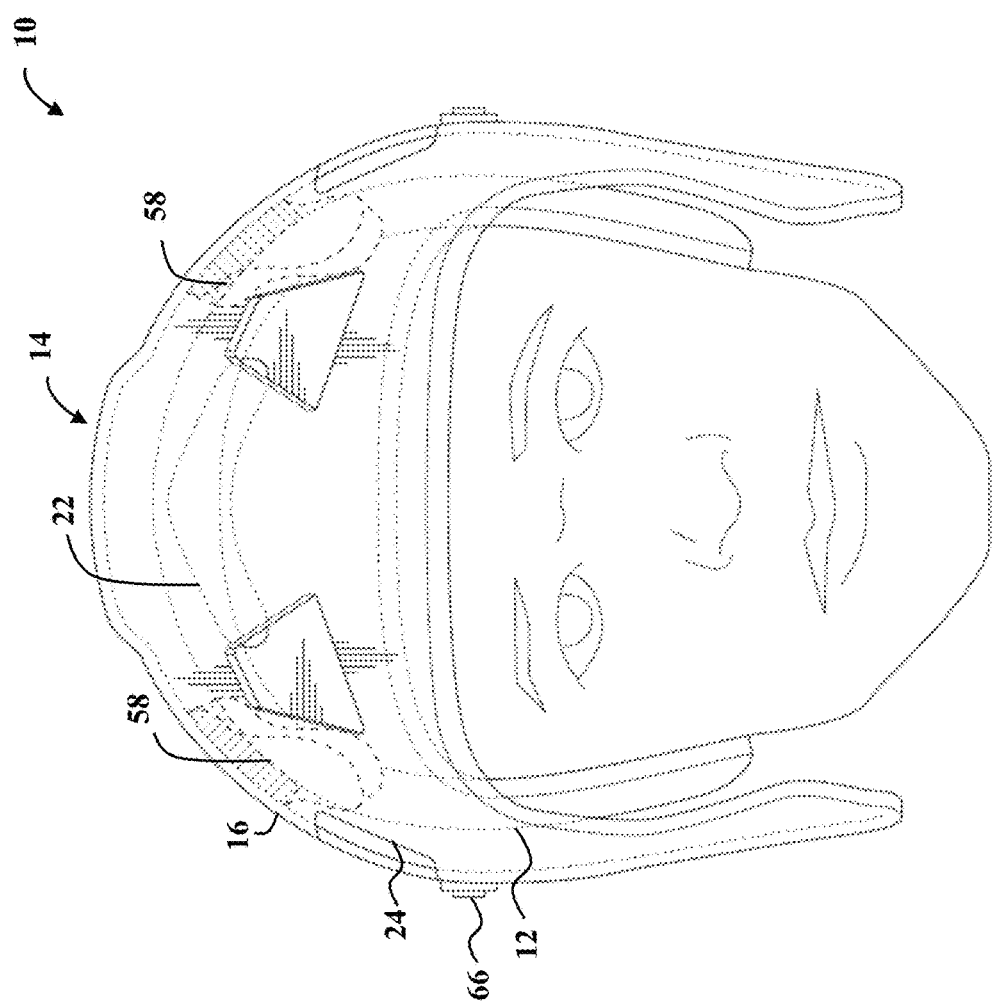
FIG. 14 is a front view of the ventilated modular helmet system of FIG. 1 with only the optional cushions in place.

In one embodiment, with reference to FIG. 6, the VMS 10 may include a plurality of cushions 52 that are coupled to the inner surface 30 of the outer shell 16 and are positioned within the climatic zone 20. The cushions 52 may also be coupled to the outer surface 26 of the inner shell 12 (not shown). The climatic zone 20 may also include only the plurality of cushions 52 that are coupled to the outer shell 16. Illustrated in FIGS. 10 and 12, each cushion 52 has a height H2, a length L3, and a width W2. The height H2 is measured along the y-axis and is defined by the distance between the end 54 of the cushion 52 that is coupled to the inner surface 30 of the outer shell 16 and the end opposite 56 the side coupled to the outer shell 16. The height H2 may vary depending on the goals of the VMS system 10. At least one cushion of the plurality of cushions 52 includes a height that is different than the height of at least one cooling packet of the plurality of cooling packets 42. The length L3 is the distance of the cushion that runs parallel to the outer shell 16 along the x-axis. The width W2 is the thickness of the cushion 52 that extends along the z-axis. The H2, L3, and W2 allow the plurality of cushions 52 to protect the cooling packets 42 by preventing the cooling packets 42 from exploding when the VMS 10 comes into contact with large forces, such as a helmet to helmet impact. The thickness, number of cushions, and position of the cushions may vary. The height H2 of the cushions 52 may be less than or equal to the length L1 of the climatic zone 20. The plurality of cushions 52 may also be a plurality of optional cushions 58, illustrated in FIGS. 13 and 14 that may be removed or placed throughout the climatic zone 20 and placed in a predetermined slot (not shown) that may help secure the optional cushion 58, shown in FIGS. 13 and 14. The plurality of cushions 58 may be optionally coupled to the outer shell 16 allowing them to be removed and replaced. The activity the VMS 10 is being used in conjunction with, may determine the need for the use of the plurality of cushions 52.

The plurality of cushions 52 may include an absorptive material. The absorptive material may be any known elastic or viscoelastic material such as, but not limited to, gels, open cell foam, close cell foam, vinyl nitrile, Styrofoam™, rubber, neoprene, foamed polymers, polyurethane foam, latex foam, micro cellular urethane foam (MCUF) or a viscoelastic foam, or any other elastic viscoelastic material having a force absorbing spring-like response. The absorptive material may be a material that can undergo a large elastic deformation in a quick period of time and has a rather slow elastic response, but may eventually return to the original shape. The distribution of forces applied to the plurality of cushions 52 under a flexible shell may be more locally realized.

In one embodiment, the ventilated modular system 10 may also include an accelerometer, a Piezometer, and/or similar devices 60. The accelerometer, Piezometer, or similar devices 60 are placed within the climatic zone 20. As shown in FIG. 6, each device 60 has a predetermined height H3, a predetermined length L4, and a predetermined width W3. The height H3 is measured along the y-axis and is defined by the distance between the end 62 of the device 60 that is coupled to the inner surface 30 of the outer shell 16 and the end 64 opposite the side coupled to the outer shell 16. The height H3 may vary depending on the goals of the VMS system 10. The length L4 is the distance of the device 60 that runs parallel to the outer shell 16 along the x-axis. The width W2 is the thickness of the device 60 that extends along the z-axis. These devices allow the measurement of the forces the helmet receives, and therefore the forces the player has been exposed to. This embodiment allows for the evaluation of an athlete immediately if the athlete has been exposed to a force exceeding a predetermined level. For example, the VMS 10 may be able to measure the impact on the athlete's head and record whether the forces extended on the helmet amount to the amount of force for a concussion or not. This embodiment may limit the amount of players continuing to play after receiving a concussion providing safety measures for the players of high impact sports, such as, but not limited to hockey, football, and/or lacrosse.

Figure 16:
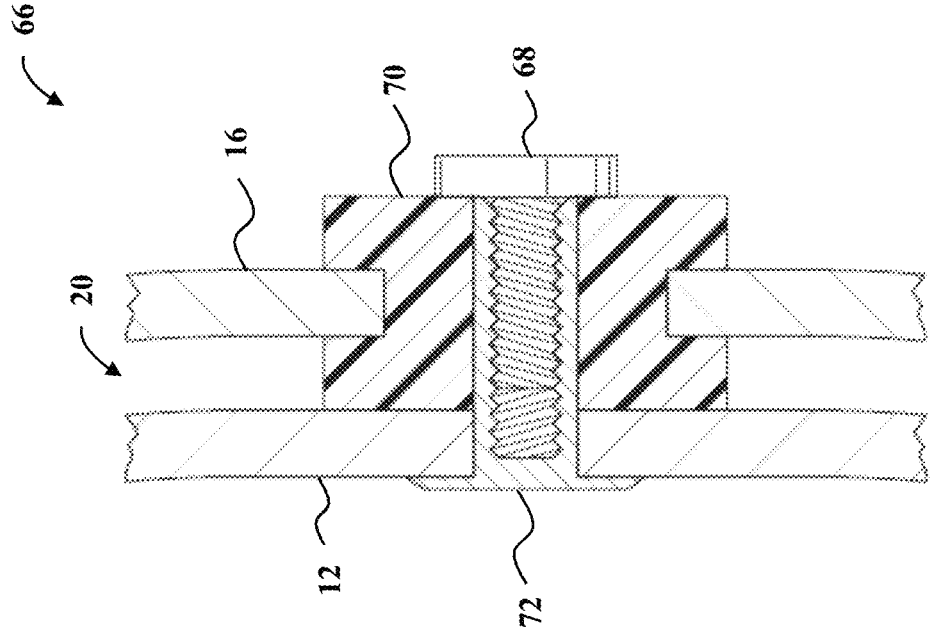
FIG. 16 is a cross-sectional view of the attachment mechanism shown in FIG. 15, and taken along section line 10-10.
Figure 17:
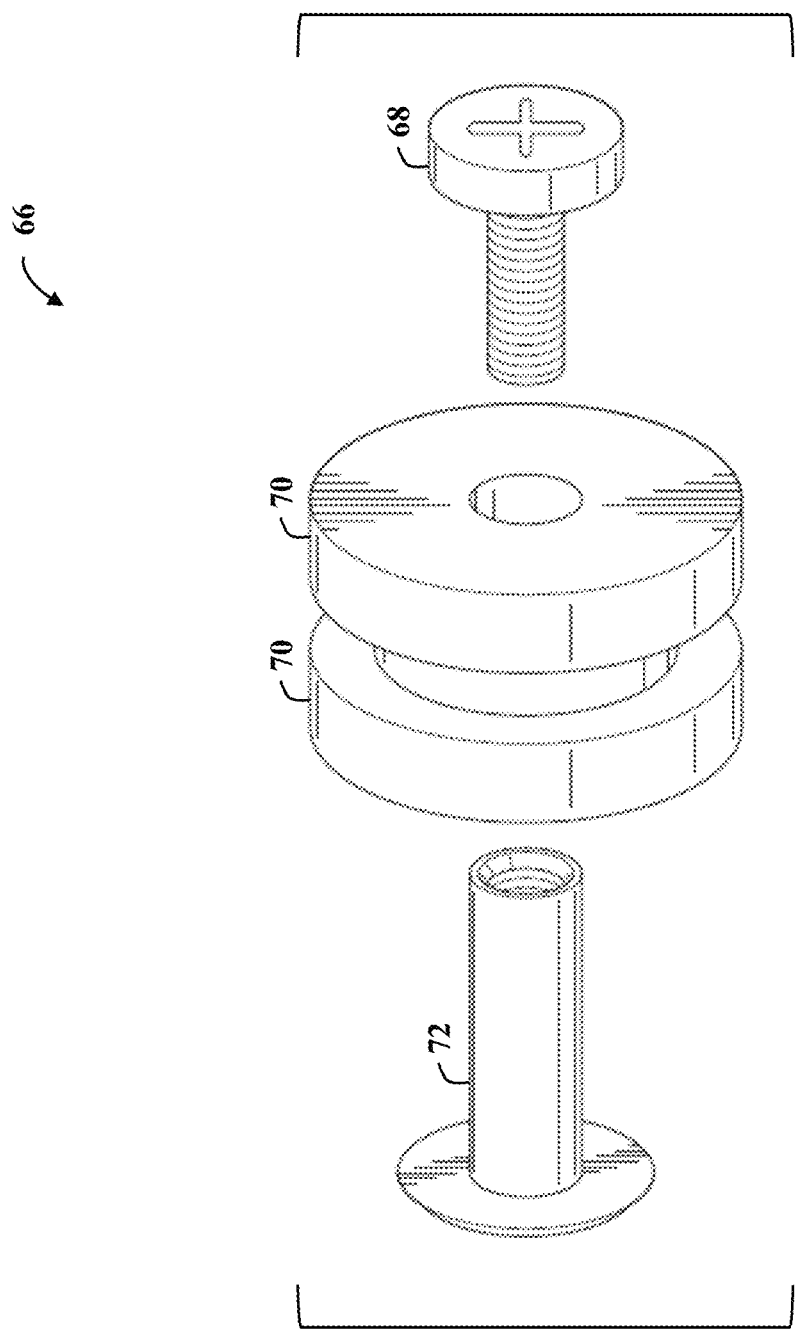
FIG. 17-26 illustrate various embodiments of the attachment mechanism of the ventilated modular helmet.

The VMS 10 also includes an attachment mechanism 66 coupled to the inner shell 12 and the outer shell 16, as shown in FIGS. 16 and 17. The VMS 10 may include a plurality of attachment mechanisms 66. The attachment mechanism 66 allows the outer shell 16 to be removably coupled to the inner shell 12. This allows the outer shell 16 to be removed and the configuration of placing the cooling packets 42 and/or the plurality of cushions 52 in any desired position within the climatic zone 20.

Figure 15:
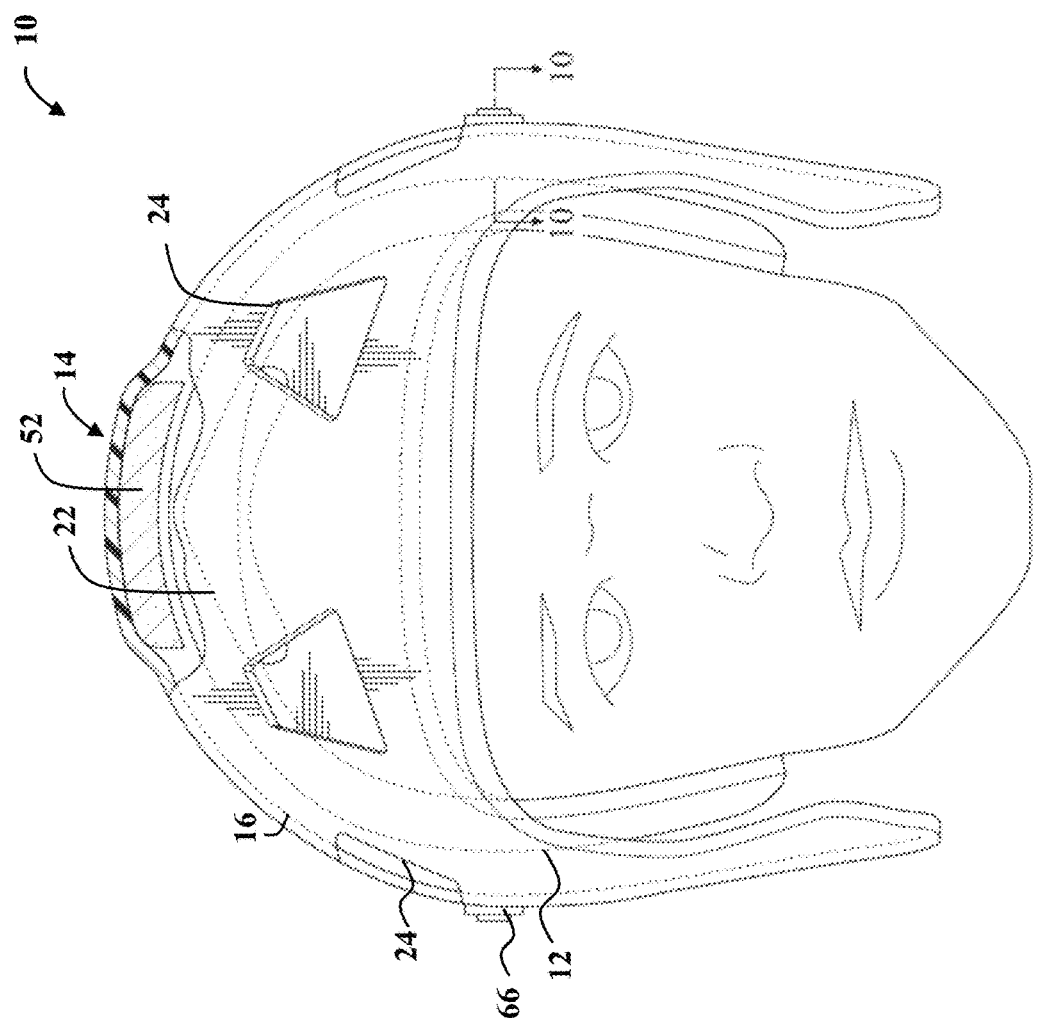
FIG. 15 is a front view of another embodiment of the ventilated modular helmet system of FIG. 13 in accordance with the teachings of the present disclosure.

As illustrated in FIGS. 16 and 17, the attachment mechanism 66 may exist in a variety of configurations, including but not limited to a rigid configuration, a flexible configuration, or a combination of both. In one embodiment, the attachment mechanism includes a fastener 68, a plurality of flexible gaskets 70, and a rigid sleeve 72. For example, as illustrated in FIGS. 16 and 17, a rigid configuration of the fastener 68, such as a screw, extends off a chinstrap snap (shown in FIG. 15) allowing rotation in one plane or no rotation at all. The fastener 68 attaches to the rigid sleeve 72 through the flexible gasket 70 to secure the inner shell 12 to the outer shell through the chinstrap opening. The flexible gasket 70 may allow the outer shell 16 to move in all planes. The flexible gasket 70 may include various densities to accommodate the player position. The rigid sleeve 72 extends through the flexible gasket 70, which extends through the outer shell 16 and the inner shell 12 securing the inner shell 12 to the outer shell 16. For example, the rigid sleeve 72 may be a t-bolt that anchors the inner shell 12, the outer shell 16, the flexible gasket 70, and the fastener 68 together. The rigid sleeve 72 may allow movement of the outer shell 16 in only one plane. In addition, the attachment mechanism 66 may be a flexible attachment such as, but not limited to, nylon or plastic, which allows a varying degree of movement in all planes. The attachment mechanism may also be a combination of both a rigid attachment surrounded by a flexible material. The attachment mechanism 66 may be configured to an individual's level of play and position of play. For example, a youth football players VMS 10 may be more flexible than a professional football players VMS 10. The attachment mechanism 66 plays a significant role in the dissipation of rotational forces. The attachment mechanism 66 may be similar to a traditional screw attachment or a quick release attachment. The kind of attachment used may be determined by the goals trying to be achieved. In addition, the attachment mechanism 66 is optional to the VMS 10. The attachment mechanism 66 allows the inner shell 12 and the outer shell 16 to be fixed optionally or permanently. This may be done with the use of a permanent attachment mechanism 74. The permanent attachment mechanism 74 uses a material, such as, an adhesive that fixes the inner shell 12 and the outer shell 16 together (not shown).

In another embodiment, illustrated in FIGS. 18-26, the attachment mechanism 66 includes a fastening assembly 76 and a fastening device 78. In one embodiment of the VMS 10, the VMS includes the inner shell 12, the outer shell 16, the fastening assembly 76, and the fastening device 78. The inner shell 12 is adapted to be positioned about a user's head. The outer shell 16 is spaced radially outwardly from the helmet inner shell. The fastening assembly 76 is configured to pivotably couple the inner shell 12 and the outer shell 16 to enable the outer shell 16 to move with respect to the inner shell 12.

The inner shell 12 includes the inner surface 24, the outer surface 26, and a plurality of inner support openings 80. Each inner support opening 80 includes a plurality of support inner surfaces 82 that extend inwardly from the outer surface 26 and outwardly from the inner surface 24. The support inner surface 82 includes a top edge 84 and a bottom edge 86. The top edge 84 is oriented obliquely with the inner surface 24 and the bottom edge 86 is oriented obliquely with the outer surface 26. The support inner surface 82 is further positioned between the inner surface 24 and the outer surface 26 such that the inner support opening 80 is defined between the inner surface 24, the outer surface 26, and the plurality of support inner surfaces 82. The inner support opening 80 is further defined as an inner cavity 88 between a first inner surface 90 and a second inner surface 92 positioned opposite the first inner surface 90. The inner cavity 88 extends through the helmet inner shell 12 from the climatic zone 20 to the user's head. In addition, the inner cavity 88 or the inner support opening 80 includes a length L5 measured between the first inner surface 90 and the second inner surface 92.

The outer shell 16 has inner surface 30, the outer surface 32, and a plurality of outer support openings 94. Each outer support opening 94 includes a plurality of support inner surfaces 96 that extend inwardly from the outer surface 32 and outwardly from the inner surface 30. The support inner surface 96 includes a top edge 98 and a bottom edge 100. The top edge 98 is oriented obliquely with the outer surface 32 and the bottom edge 100 is oriented obliquely with the inner surface 30. The support inner surface 96 is positioned between the outer surface 32 and the inner surface 30 such that the outer support opening 94 is defined between the outer surface 32, the inner surface 30, and the plurality of support inner surfaces 96. The outer support opening 94 is further defined as an outer cavity 102 between a first support inner surface 104 and a second support inner surface 106 positioned opposite the first support inner surface 104. The outer cavity 102 through the helmet outer shell 16 from the outside the helmet outer shell 16 to the climatic zone 20. In addition, the outer cavity 102 and/or the outer support opening 96 includes a length L6 measured between the first support inner surface 104 and the second support inner surface 106. The outer support opening length L6 can be the same of different than the length L5 of the inner support opening.

Illustrated in FIGS. 18-23, the fastening assembly 76 includes an outer support member 108, an inner support member 110, a base member 112, a protective plate 114, and at least one positioning opening 116. The fastening assembly 76 acts similar to the attachment mechanism 66 described above, but also allows the outer shell 16 to resist a rotation that is independent of the inner shell 12 in all planes. The fastening assembly 76 may include a material such as thermoplastic polyurethane or polyvinyl nitrile, or any material that includes the desired properties.

Figure 20:
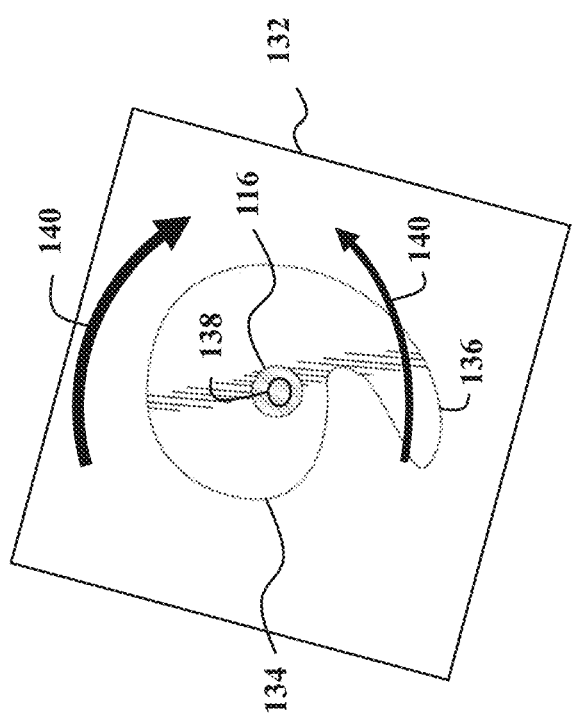
Figure 21:
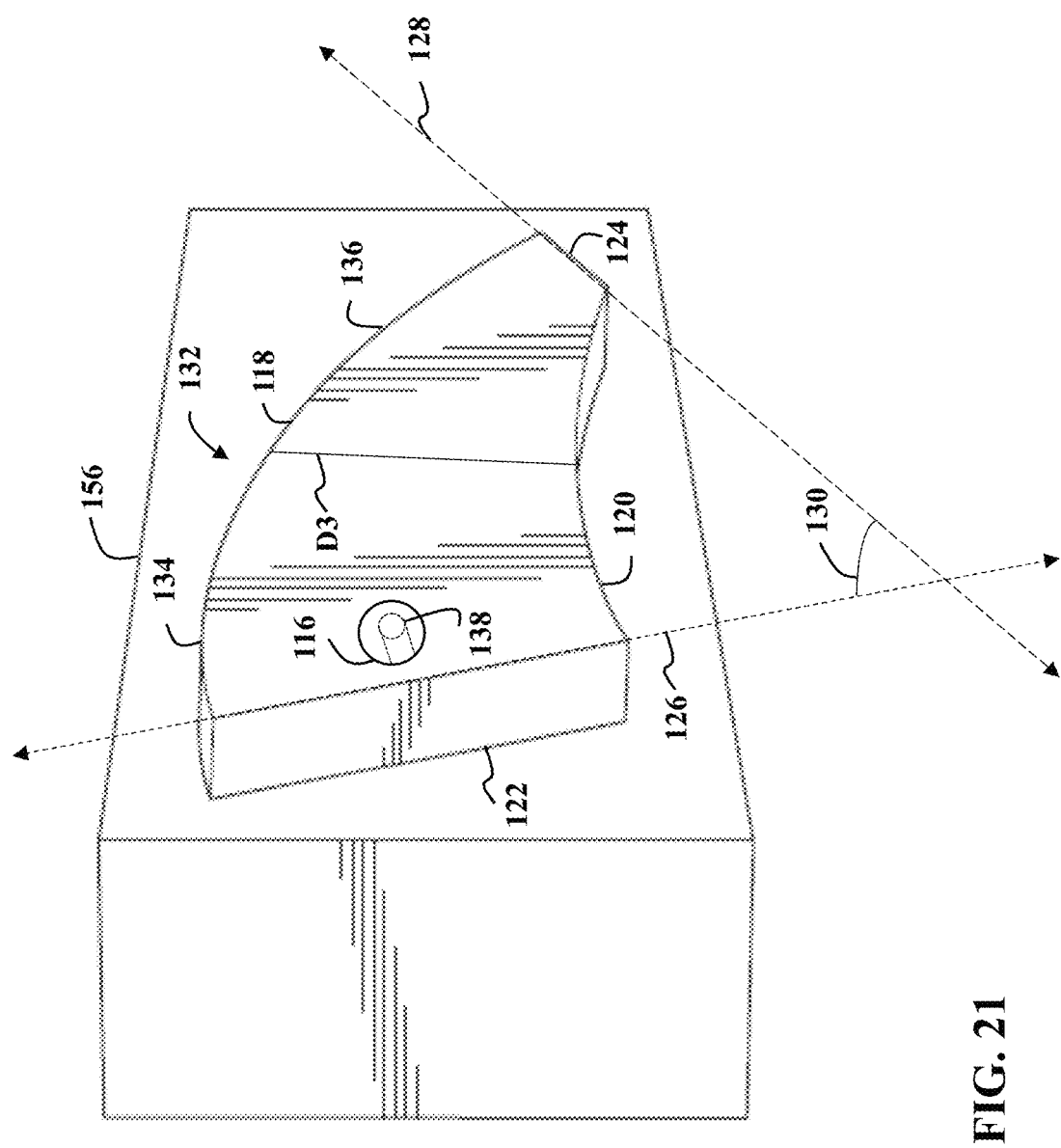
Figure 22:
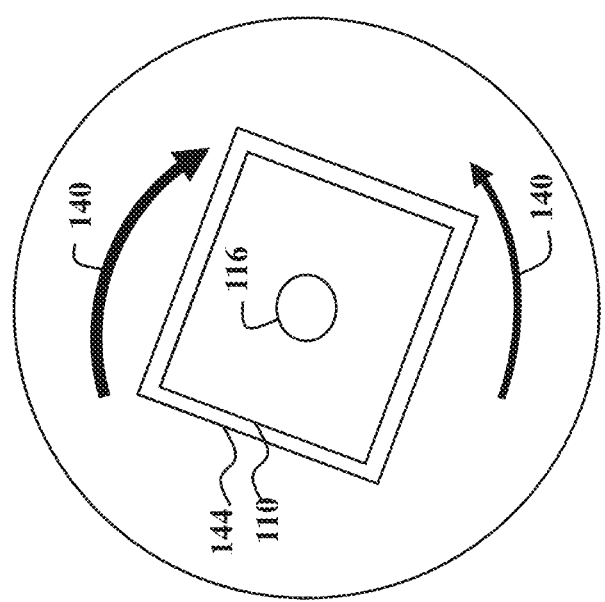
Figure 23:
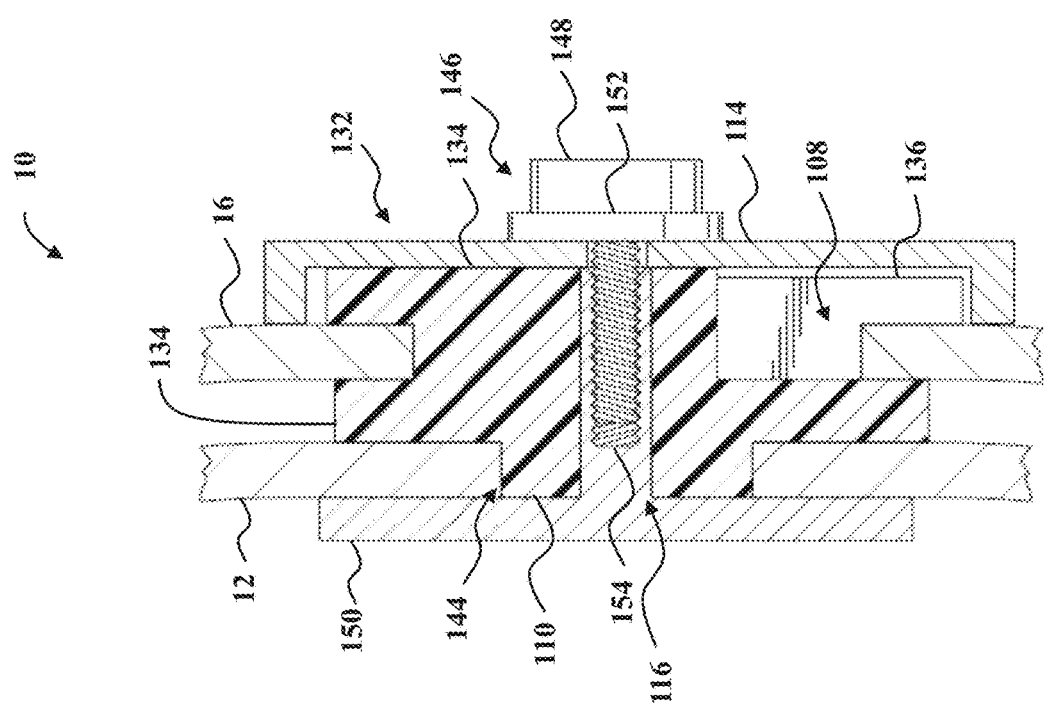

In one embodiment, the outer support member 108 includes a non-uniform cross-sectional shape. In addition, the outer support opening 94 may include a shape that is substantially similar to the shape of the outer support member 108. For example, as shown in FIG. 20, the outer support member 108 may include a non-uniform cross-sectional shape resembling a Figure "9". In another embodiment, as shown in FIG. 21, the outer support member 108 may include a non-uniform cross-sectional shape having an elongated body including a plurality of arcuate surfaces. In addition, the outer support member 108 may include any shape having the desired physical properties. Referring to FIG. 21, in one embodiment, the outer support member 108 includes an arcuate top 118 and an arcuate bottom 120 and a first planar side 122 and a second planar side 124. The arcuate top 118 and the arcuate bottom 120 have a predetermined distance D3 that varies between the first planar side 122 and the second planar side 124. The first planar side 122 is parallel to a first plane 126, and the second planar side 124 is parallel to a second plane 128. The first plane 126 and the second plane 128 form an oblique angle 130.

Figure 19:
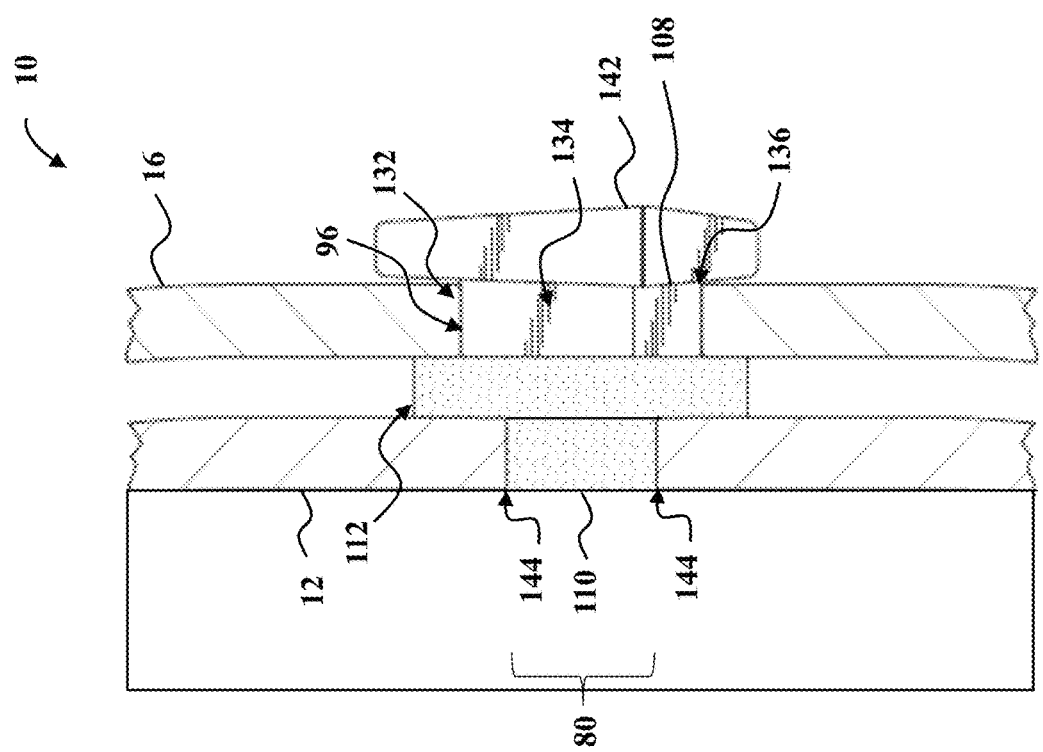

In the illustrated embodiment, as shown in FIG. 19, the outer support member 108 includes a support body 132 that is sized and shaped to be inserted through the outer support opening 94 of the outer shell 16. The support body 132 includes a base portion 134 and a support arm 136. The base portion 134 includes a pivot axis 138, and the support arm 136 extends outwardly along the y-axis from the base portion 134. The outer support member 108 is positioned within the outer support opening 94 extending through the helmet outer shell 16 such that the outer surface of the support arm 136 contacts the inner surface 96 of the outer support opening 94 to facilitate resisting a rotation 140 of the helmet outer shell 16 about the pivot axis 138. In one embodiment, the outer support member 108 includes a support flange 142 extending outwardly from the support body 132. The support flange 142 is sized and shaped to contact the outer surface 32 of the outer shell 16 to facilitate coupling the fastening assembly 76 to the outer shell 16.

In the illustrated embodiment, the inner support member 110 extends outwardly from the outer support member 108 towards the user's head. The inner support member 110 is positioned within the inner support opening 80 of the inner shell 12. The inner support member 110 includes an outer surface 144 that is sized and shaped to contact the inner surface 82 of the inner support opening 80 to facilitate resisting a rotation of the outer support member 108 about the pivot axis 138. In one embodiment, the inner support member 110 includes a substantially uniform cross-sectional shape such as for example, a square. In another embodiment, the inner support member 110 includes any shape having the desired physical properties. The inner support member 110 is positioned within the inner support opening 80 extending through the helmet inner shell 12 such that the outer surface 144 of the inner support member 110 is configured to contact the inner surface 82 of the inner support opening 80 to facilitate resisting a rotation of the outer support member 108 about the pivot axis 138.

The base member 112 is coupled between the inner support member 110 and the outer support member 108 and is positioned within the gap formed between the helmet inner shell 12 and the helmet outer shell 16. In the illustrated embodiment, the base member 112 includes a cross-sectional area that is greater than the cross-sectional area of the outer support member 108 and/or the inner support member 110 to facilitate coupling the inner shell 12 to the outer shell 16.

The protective plate 114 includes an inner surface that defines a cavity that is sized and shaped to receive a portion of the outer support member 108 therein. The protective plate 114 is positioned adjacent the outer surface 32 of the outer shell 16 and adapted to encapsulate the outer support member 108 within the cavity. In one embodiment, the fastening device 78 is inserted through an opening 116 extending through the protective plate 114 to facilitate coupling the protective plate 114 to the outer surface 32 of the outer shell 116.

Figure 24:
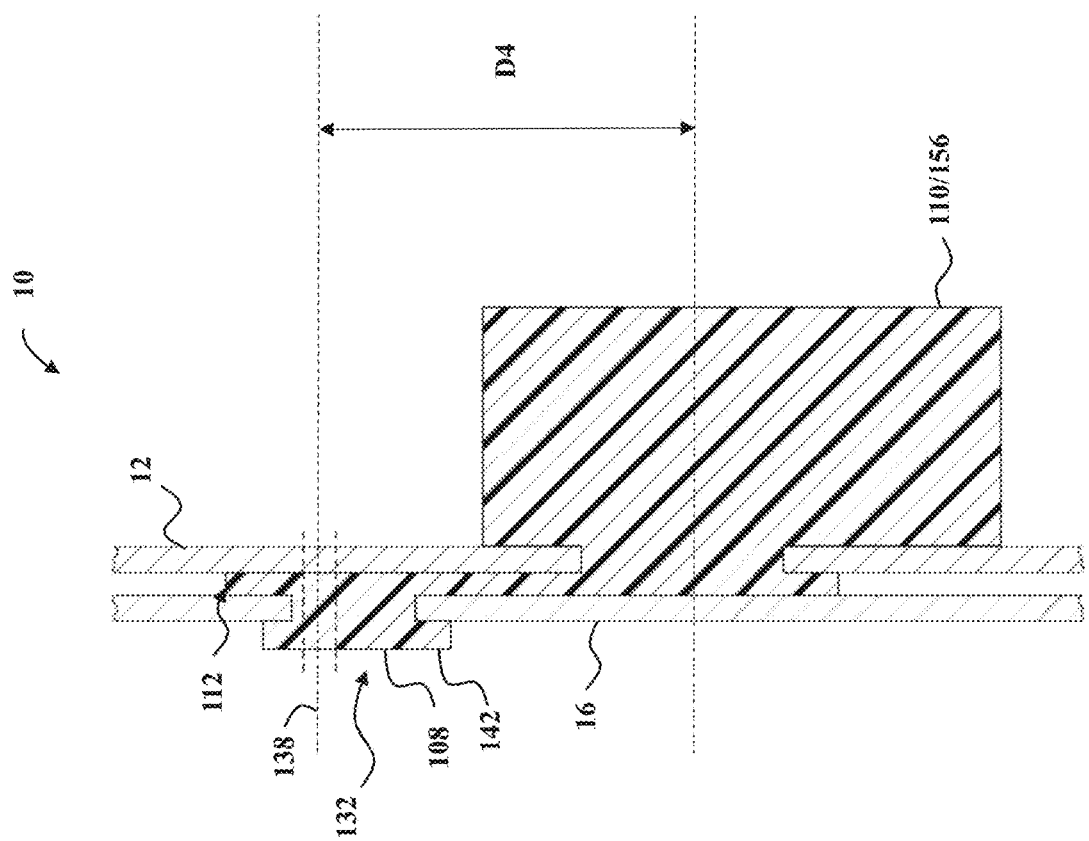
Figure 25:
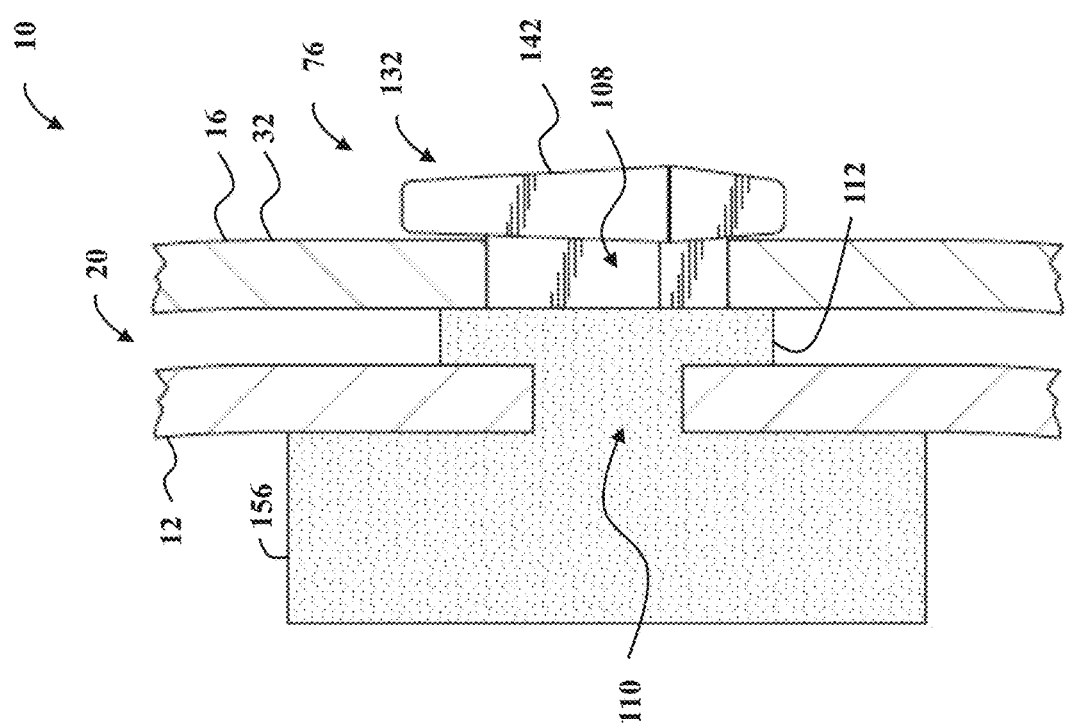

In the illustrated embodiment, the fastening assembly 76 includes the positioning opening 116 extending through the outer support member 108, the base member 112, and the inner support member 110, and orientated along the pivot axis 138. The fastening device 78 is positioned within the positioning opening 116 and configured to couple the fastening assembly 76 to the inner shell 12 and the outer shell 16. In one embodiment, as shown in FIG. 24 the inner support member 110 is spaced a distance D4 from the pivot axis 138 defined by the base portion, and the positioning opening 116 extends through the outer support member 108, the base member 112, and the inner shell 12.

Figure 18:
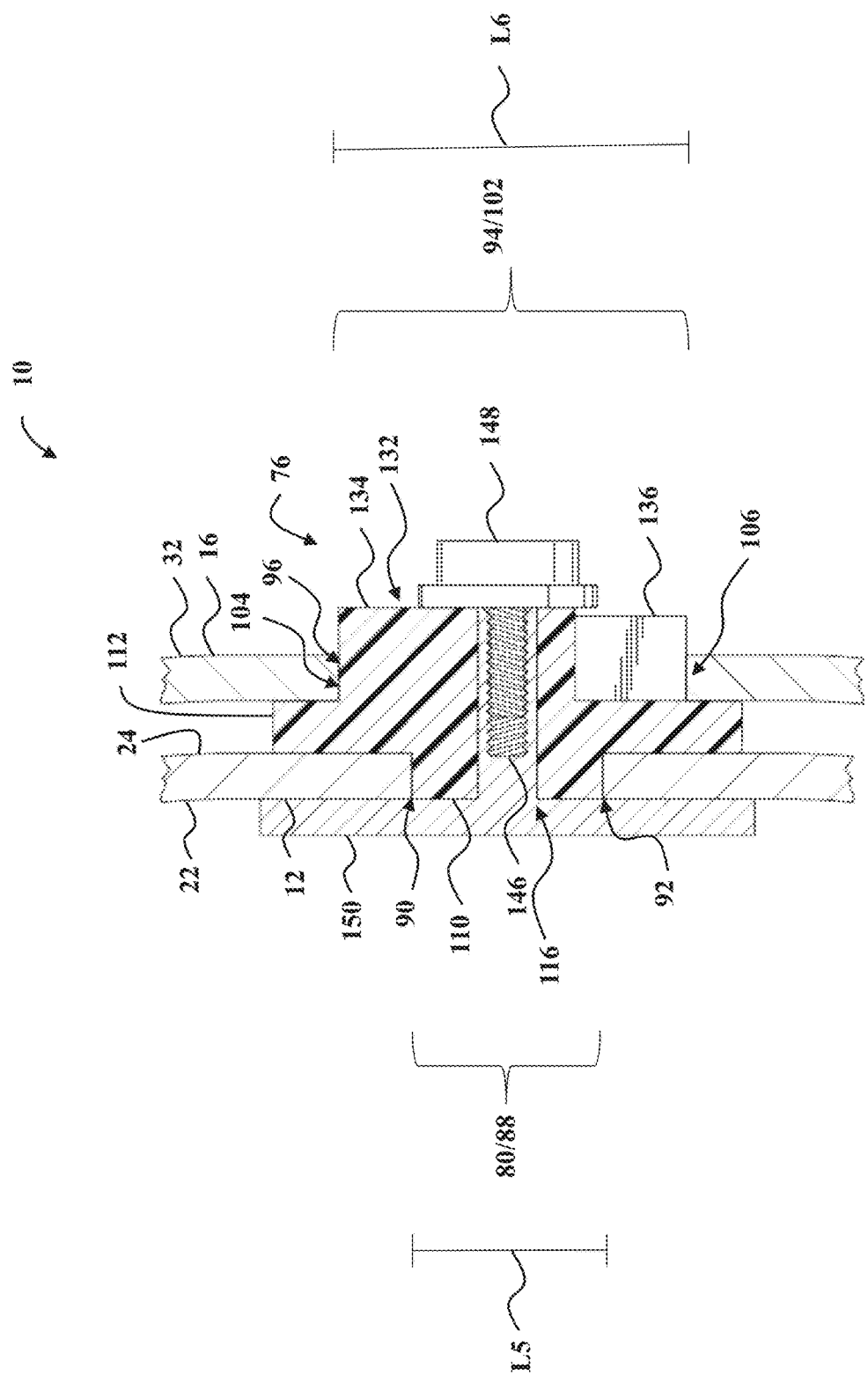

As shown in FIG. 18, in one embodiment, the fastening device 78 includes a fastener 146, a snap access 148, and a rigid sleeve 150. The fastening device 78 is coupled to the fastening assembly 76 and the helmet inner shell 12. The fastener 146 has a top portion 152 and a bottom portion 154. The fastener 146 has a shape that may include but is not limited to a screw or any shape having the desired physical properties. The snap access 148 has a shape that may include but is not limited to two stacked cylinders or any shape having the desired physical properties, for example a shape that accepts a chin strap snap. The rigid sleeve 150 has a shape that may include but is not limited to a t-bolt or any shape having the desired physical properties.

In yet another embodiment, the VMS 10 includes an inner cushion 156 that interacts with the inner shell 12 and the fastening assembly 76 to protect the skull or head of the user.

The inner cushion 156 extends outwardly from the outer support member 108 towards a user's head. The inner cushion 156 is configured to contact the user's head to facilitate resisting a rotation of the outer support member 108 about the pivot axis 138. In one embodiment, inner cushion 156 is similar to the cushions within the cooling assembly 18.

Figure 26:
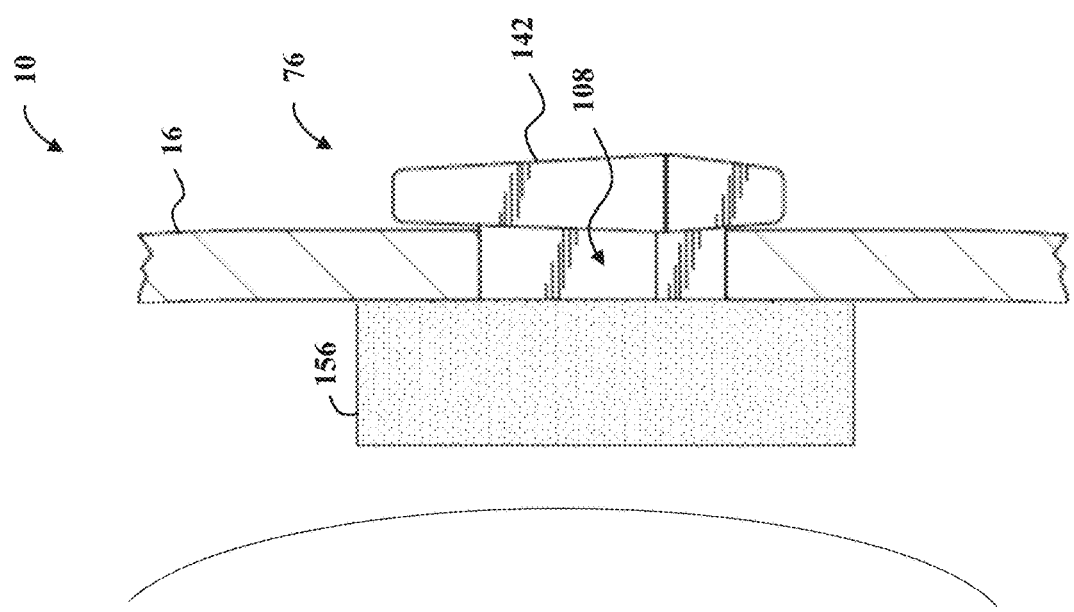
Figure 27:
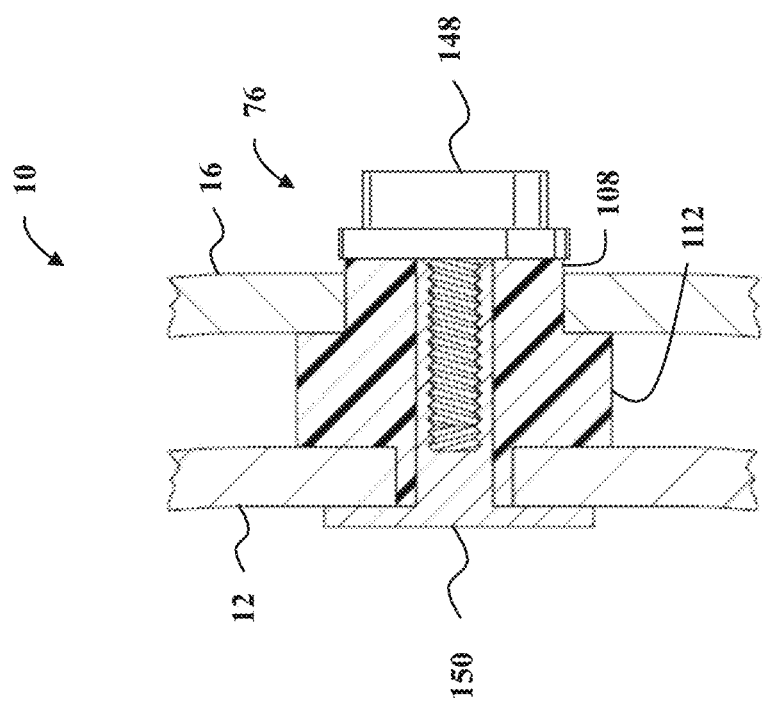
FIG. 27 illustrates a perspective view of the fastening assembly within the ventilated modular helmet.
Figure 29:
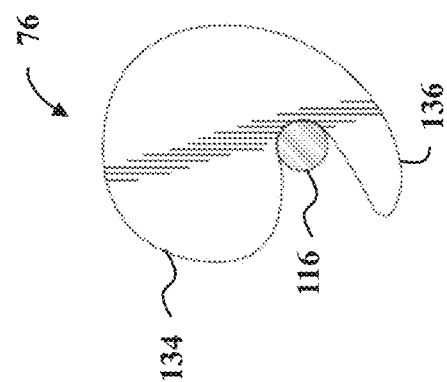
FIG. 29 illustrates a front view of the outer support member of the ventilated modular helmet.
Figure 28:
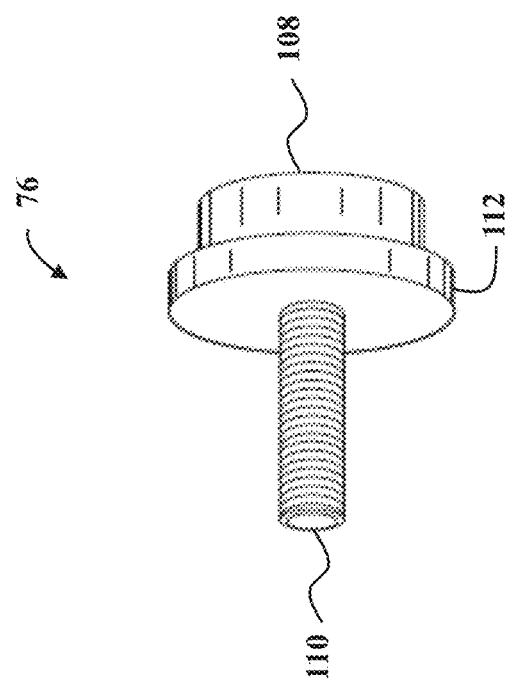
FIG. 28 illustrates a perspective view of the fastening assembly of the ventilated modular helmet.
Figure 31:
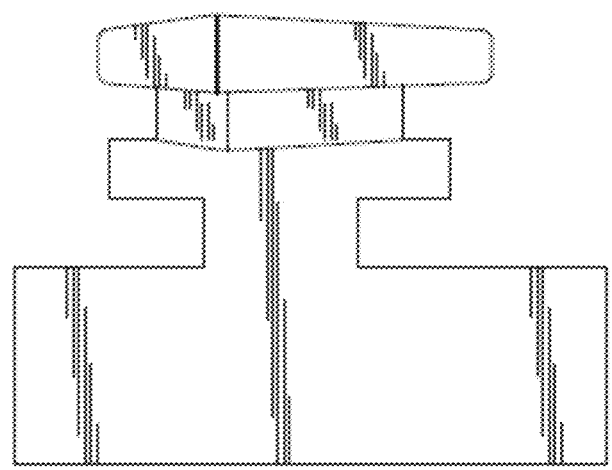
FIG. 31 illustrates a front view of the attachment mechanism of the ventilated modular helmet.
Figure 30:
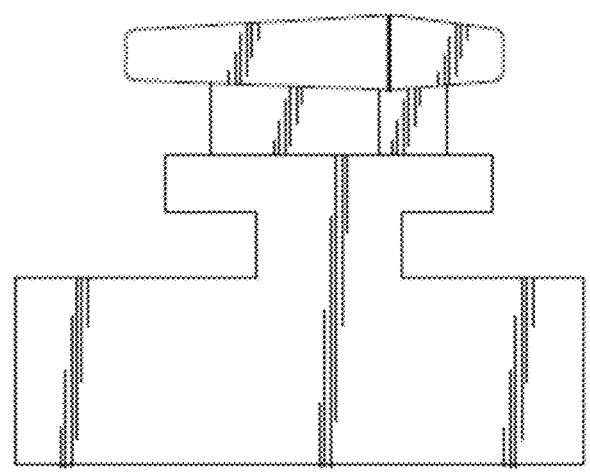
FIG. 30 illustrates a top view of the attachment mechanism of the ventilated modular helmet.

In one embodiment, as shown in FIG. 26, the VMS 10 may not include the helmet inner shell 12 or the fastening device 78. This may allow the inner cushion 156 to act as the inner support member 110 and resist the rotation of the outer support member 108. The inner cushion 156 is positioned within the gap between the outer shell 16 and the user's head.

The ventilated modular system 10 may include a first shell having an outer surface, a second shell outward of the outer surface of the first shell and offset distance, a layer disposed between the outer surface of the first shell and the second shell which may contain absorptive material, a coolant material, padding, and air layer, or any combination of these materials and an attachment mechanism to couple the second shell to the first shell. The second shell may be permanently or temporarily coupled to the first shell. The second shell may be outward of the first shell by a variable distance determined by the materials used in the layer disposed between the outer surface of the first shell and the second shell. The second shell may have a portion which is removable and replaceable with respect to the first shell. The first shell maybe rigid, semi-rigid, or flexible. The second shell may be rigid, semi-rigid, or flexible. The first shell may contain vents, pores or a combination of both. These vents and pores may be of any size and be located at any position. The second shell may contain vents, pores or a combination of both. These vents and pores may be of any size and be located at any position. In the event the second shell is rigid, it may have a thickness which fractures upon application of a particular force, the particular force may be less than or equal to a predetermined threshold force at which a user should undergo further evaluation.

The ventilated modular system 10 may include the middle layer or climatic layer including a uniform thickness, or alternatively different thicknesses of different areas of the shell, for example at the top of the second shell in the side of the second shell. The ventilated modular system may also include one or more cushions, coolant packs, or desiccant packs strategically positioned. These components may be located underneath the second shell or they may be coupled to the second shell, wherein the component may include a cover layer. The one or more components may be strategically positioned at various locations between the first and second shells. The components may be used in conjunction with an accelerometer, piezometer, or similar devices between the first and second shells. The components may be customizable to one of the level of play and the size of the player. These aspects are merely illustrative on innumerable aspects associated with the present invention and should not be deemed as limiting in any manner. These and other aspects, features and advantages of the present invention will become apparent from the following detailed description when taken in conjunction with reference drawings.

The present invention has been described in an illustrative manner. It is to be understood that the terminology, which has been used, is intended to be in the nature of words of description rather than of limitation.

Many modifications and variations of the present invention are possible in light of the above teachings. Therefore, the present invention may be practiced other than as specifically described.

What is claimed is:

1. A modular helmet comprising:
   an inner shell adapted to be positioned onto a user's head;
   an outer shell coupled to the inner shell, the outer shell spaced a distance radially outward from the inner shell to define a climatic zone between the inner shell and the outer shell; and
   a cooling assembly positioned within the climatic zone between the inner shell and the outer shell, the cooling assembly including a plurality of cooling packets that are coupled to the outer shell; and
   a plurality of cushions that are coupled to the outer shell and positioned within the climatic zone.

2. The modular helmet of claim 1, wherein at least one cushion of the plurality of cushions includes a height that is different than a height of at least one cooling packet of the plurality of cooling packets.

3. A modular helmet comprising:
   an inner shell adapted to be positioned onto a user's head;
   an outer shell coupled to the inner shell, the outer shell spaced a distance radially outward from the inner shell to define a climatic zone between the inner shell and the outer shell; and
   a cooling assembly positioned within the climatic zone between the inner shell and the outer shell, the cooling assembly including a plurality of cooling packets that are coupled to the outer shell, wherein the inner shell includes a plurality of inner vents configured to couple the climatic zone in flow communication with an area adjacent the users head.

4. The modular helmet of claim 3, wherein the outer shell includes a plurality of outer vents configured to couple the climatic zone in flow communication with ambient air.

5. The modular helmet of claim 4, wherein at least one inner vent is orientated coaxially with a corresponding outer vent.

6. The modular helmet of claim 1, further including an attachment mechanism coupled to the inner shell and the outer shell, wherein the outer shell is removably coupled to the inner shell.

7. A modular helmet comprising:
   an inner shell adapted to be positioned onto a user's head, the inner shell includes a plurality of inner vents;
   an outer shell coupled to the inner shell, the outer shell spaced a distance radially from the inner shell to define a climatic zone between the inner shell and the outer shell, the outer shell includes a plurality of outer vents configured to couple the climatic zone in flow communication with ambient air; and
   a cushion assembly positioned within the climatic zone between the inner shell and the outer shell, the cushion assembly including a plurality of cushions that are coupled to the outer shell.

8. The modular helmet of claim 7, including a plurality of cooling packets that are coupled to the outer shell and positioned within the climatic zone.

9. The modular helmet of claim 8, wherein at least one cushion of the plurality of cushions includes a height that is different than a height of at least one cooling packet of the plurality of cooling packets.

10. The modular helmet of claim 7, wherein the plurality of inner vents includes a first amount of inner vents and the plurality of outer vents includes a second amount of outer vents that is a different than the first amount of inner vents.

11. The modular helmet of claim 7, further including an attachment mechanism coupled to the inner shell and the outer shell, wherein the outer shell is removably coupled to the inner shell.

12. A fastening assembly for use with a helmet assembly including an outer shell, the fastening assembly comprising:
   an outer support member adapted to be positioned within a support opening extending through the outer shell, the outer support member including a base portion defining a pivot axis and a support arm extending outwardly from the base portion, the support arm configured to contact an inner surface of the support opening to facilitate resisting a rotation of the helmet outer shell about the pivot axis, wherein helmet assembly includes a helmet inner shell that is spaced radially inward from the helmet outer shell and adapted to be positioned about a user's head, the fastening assembly including an inner support member extending outwardly from the outer support member towards the user's head, the inner support member positioned within an inner support opening extending through the helmet inner shell.

13. The fastening assembly of claim 12, wherein the support opening includes a shape that is substantially similar to a shape of the outer support member.

14. The fastening assembly of claim 12, wherein the inner support member includes an outer surface in contact with an inner surface of the inner support opening to facilitate resisting a rotation of the outer support member about the pivot axis.

15. The fastening assembly of claim 14, wherein the fastening assembly includes a base member between the inner support member and the outer support member, the base member positioned within a gap defined between the helmet inner shell and the helmet outer shell.

16. The fastening assembly of claim 15, wherein the inner support member is spaced a distance from the pivot axis defined by the base portion.

17. The fastening assembly of claim 15, further comprising:
   a positioning opening extending through the outer support member, the base member, and the inner support member, and orientated along the pivot axis; and
   a fastening device positioned within the positioning opening and configured to couple the fastening assembly to the inner and outer shells.

18. The modular helmet of claim 3, further including an attachment mechanism coupled to the inner shell and the outer shell, wherein the outer shell is removably coupled to the inner shell.

* * * * *

(12) INTER PARTES REVIEW CERTIFICATE (2984th)
United States Patent (10) Number: US 10,617,167 K1
Baldi (45) Certificate Issued: Jan. 25, 2023

(54) VENTILATED MODULAR DUAL SHELLED HELMET SYSTEM

(71) Applicant: Steven T. Baldi

(72) Inventor: Steven T. Baldi

(73) Assignee: APALONE, INC.

Trial Number:

IPR2022-00196 filed Nov. 15, 2021

Inter Partes Review Certificate for:

Patent No.: 10,617,167
Issued: Apr. 14, 2020
Appl. No.: 15/820,256
Filed: Nov. 21, 2017

The results of IPR2022-00196 are reflected in this inter partes review certificate under 35 U.S.C. 318(b).

INTER PARTES REVIEW CERTIFICATE
U.S. Patent 10,617,167 K1
Trial No. IPR2022-00196
Certificate Issued Jan. 25, 2023

AS A RESULT OF THE INTER PARTES REVIEW PROCEEDING, IT HAS BEEN DETERMINED THAT:

Claims 1-11 and 18 are cancelled.

\* \* \* \* \*